US009090678B2

(12) United States Patent
Gronthos et al.

(10) Patent No.: US 9,090,678 B2
(45) Date of Patent: Jul. 28, 2015

(54) MONOCLONAL ANTIBODY STRO-4

(75) Inventors: Stan Gronthos, Adelaide (AU); Andrew Christopher Williem Zannettino, Highbury (AU)

(73) Assignee: MESOBLAST, INC., New York, NY (US)

(*) Notice: Subject to any disclaimer, the term of this patent is extended or adjusted under 35 U.S.C. 154(b) by 97 days.

(21) Appl. No.: 13/059,448

(22) PCT Filed: Aug. 18, 2009

(86) PCT No.: PCT/AU2009/001060
§ 371 (c)(1),
(2), (4) Date: Apr. 15, 2011

(87) PCT Pub. No.: WO2010/019997
PCT Pub. Date: Feb. 25, 2010

(65) Prior Publication Data
US 2011/0189696 A1    Aug. 4, 2011

Related U.S. Application Data

(60) Provisional application No. 61/189,349, filed on Aug. 18, 2008.

(51) Int. Cl.
| G01N 33/567 | (2006.01) |
| A61K 38/00  | (2006.01) |
| C12N 5/00   | (2006.01) |
| C07K 16/18  | (2006.01) |
| G01N 33/50  | (2006.01) |
| C12N 5/0775 | (2010.01) |

(52) U.S. Cl.
CPC .............. *C07K 16/18* (2013.01); *C12N 5/0663* (2013.01); *G01N 33/5044* (2013.01); *G01N 2333/4703* (2013.01)

(58) Field of Classification Search
None
See application file for complete search history.

(56) References Cited

FOREIGN PATENT DOCUMENTS

| EP | 1457499 A1       | 7/2003  |
| JP | 2006-314299      | 11/2006 |
| WO | WO 2006/032092 A1 | 3/2006  |
| WO | WO 2006/037649 A1 | 4/2006  |
| WO | WO 2006/050333   | 5/2006  |
| WO | WO 2007/093431   | 8/2007  |

OTHER PUBLICATIONS

Cid et al (J of Neurochemistry, 2005, v.95, pp. 349-360).*
Jan. 17, 2013 Written Opinion in connection with Singapore Patent Application No. 201100906-5.
Jul. 9, 2013 Response to Jan. 17, 2013 Written Opinion in connection with Singapore Patent Application No. 201100906-5.
Mar. 20, 2013 Supplementary European Search Report issued in connection with EPO Application No. 09807748.0.
Chen et al. (2007), "Isolation and Culture of rat and mouse oligodendrocyte precursor cells", *Nature Protocols* (2)5:1044-51.
Gronthos et al. (2008) "A method to Isolate and Purify Human Bone Marrow Stromal Stem Cells", *Methods in Molecular Biology*, Chapter 3, vol. 449, pp. 45-57.
Kemoun et al. (2011) "The role of cell surface markers and enamel matrix derivatives on human periodontal ligament mesenchymal progenitor responses in vitro", *Biomaterials* (32) :7375-88.
Seo et al. (2004) "Investigation of multipotent postnatal stem cells from human periodontal ligament", *The Lancet* (364):149-55.
Tsutsumi et al. (2007) "Extracellular heat shock protein 90: A role for a molecular chaperone in cell motility and cancer metastasis", *Cancer Sci.* (98)10:1536-39.
Jun. 8, 2013 Office Action issued in connection with Chinese Patent Application No. 200980141163.9.
Jan. 27, 2014 Office Action issued in connection with Japanese Patent Application No. 2011-523265 (English translation).
Cid et al., "Anti-heat shock protein 90β antibodies decrease pre-oligodendrocyte population in perinatal and adult cell cultures . . . ," J. Neurochem. 2005(95):349-360.
International Search Report issued by the International Searching Authority (ISA/AU) on Oct. 26, 2009 in connection with PCT International Application No. PCT/AU2009/001060.
Written Opinion of the International Searching Authority (ISA/AU) mailed Oct. 26, 2009 in connection with PCT International Application No. PCT/FR2009/000197.
Cid, C., Álvarez-Cermeflo, J., Salinas, M., & Alcazar, A. (2005). Anti-Heat Shock Protein 90B Antibodies Decrease Pre-Oligodendrocyte Population in Perinatal and Adult Cell Cultures. Implications for Remyelination in Multiple Sclerosis. Journal of Neurochemistry. 95, 349-360.
Cid, C., Álvarez-Cermeño, J., Salinas, Camafeita, E., Salinas, M & Alcazar, A. (2003) Antibodies Reactive to Heat Shock Protein 90 Induce Oligodendrocyte Precursor Cell Death in Culture. Implications for Demyelination in Multiple Sclerosis. The FASEB Journal express article 10.1096/fj.03-0606fje.
Yamada, T., Hashiguchi, A., Fukushima, S., Kakita, Y., Umezawa, A., Maruyama, Function of 90-kDa Heat Shock Protein in Cellular Differentiation of Human Embryonal Carcinoma Cells. In Vitro Cellular and Developmental Biology—Animal 36, 139-146, 2006.
Akama, K., Tatsuno, R., Otsu, M., Horikoshi, T., Nakayama, T., Nakamura, M.,Toda, T. & Inoue, N. (2008) Proteomic Identification of Differentially Expressed .3enes in Mouse Neural Stem Cells and Neurons Differentiated From Embryonic Stem Cells In Vitro. Biochimica et Biophysics Acta. 1784, 773-782.
Gronthos, S., McCarty, R., Mrozik, K., Fitter, S., Paton, S., Menicanin, D., Itescu, S., Bartold, P., Xian, C. & Zannettino, A. Cell Surface HSP90 is a Marker of Multipotential Mesechmyal Stromal Cells. Stem Cells and Development, 2009, v.18, 1253-62.

(Continued)

*Primary Examiner* — Michail Belyavskyi
(74) *Attorney, Agent, or Firm* — John P. White; Cooper & Dunham LLP

(57) ABSTRACT

The present invention relates to a monoclonal antibody designated STRO-4 which specifically binds human and ovine HSP-90beta and its use for enriching multipotential cells such a mesenchymal precursor cells (MPCs).

5 Claims, 6 Drawing Sheets

(56) References Cited

OTHER PUBLICATIONS

Sidera, K., Samiotaki, M., Yfanti, B., Panayotou, G. & Patsavoudi, E. (2004) Involvement of Cell Surface HSP90 in Cell Migration Reveals a Novel Role in the Developing Nervous System. The Journal of Biological Chemistry. 279, 44, 45379-45388.

PCT International Application Publication No. WO 2005/009350 A2, published Feb. 3, 2005 (The General Hospital Corporation).

Office Action issued Feb. 16, 2015 in connection with Japanese Patent Application No. 2011-523265.

Office Action issued Feb. 16, 2015 in connection with Japanese Patent Application No. 2011-523265 (English translation).

* cited by examiner

Peptide sequence for human heat shock protein-90 beta (NCBI, accession number, P08238)

Matched STRO-4 sequenced peptides are shown in Bold

```
  1 PEEVHHGEEE VETFAFQAEI AQLMSLIINT FYSNKEIFLR ELISNASDAL
 51 DKIRYESLTD PSKLDSGKEL KIDIIPNPQE RTLTLVDTGI GMTKADLINN
101 LGTIAKSGTK AFMEALQAGA DISMIGQFGV GFYSAYLVAE KVVVITKHND
151 DEQYAWESSA GGSFTVRADH GEPIGRGTKV ILHLKEDQTE YLEERRVKEV
201 VKKHSQFIGY PITLYLEKER EKEISDDEAE EEKGEKEEED KDDEEKPKIE
251 DVGSDEEDDS GKDKKKKTKK IKEKYIDQEE LNKTKPIWTR NPDDITQEEY
301 GEFYKSLTND WEDHLAVKHF SVEGQLEFRA LLFIPRRAPF DLFENKKKKN
351 NIKLYVRRVF IMDSCDELIP EYLNFIRGVV DSEDLPLNIS REMLQQSKIL
401 KVIRKNIVKK CLELFSELAE DKENYKKFYE AFSKNLKLGI HEDSTNRRRL
451 SELLRYHTSQ SGDEMTSLSE YVSRMKETQK SIYYITGESK EQVANSAFVE
501 RVRKRGFEVV YMTEPIDEYC VQQLKEFDGK SLVSVTKEGL ELPEDEEEKK
551 KMEESKAKFE NLCKLMKEIL DKKVEKVTIS NRLVSSPCCI VTSTYGWTAN
601 MERIMKAQAL RDNSTMGYMM AKKHLEINPD HPIVETLRQK AEADKNDKAV
651 KDLVVLLFET ALLSSGFSLE DPQTHSNRIY RMIKLGLGID EDEVAAEEPN
701 AAVPDEIPPL EGDEDASRME EVD
```

FIGURE 5

MONOCLONAL ANTIBODY STRO-4

This application is a §371 national stage of PCT International Application No. PCT/AU2009/001060, filed Aug. 18, 2009, and claims the benefit of U.S. Provisional Application No. 61/189,349, filed Aug. 18, 2008, which are hereby incorporated by reference in their entirety.

This application incorporates-by-reference nucleotide and/or amino acid sequences which are present in the file named "110217_2251_79689_A_PCT_US_Substitute_Sequence_Listing_D ES.txt," which is 7 kilobytes in size, and which was created Feb. 10, 2011 in the IBM-PC machine format, having an operating system compatibility with MS-Windows, which is contained in the text file filed Feb. 17, 2011 as part of this application.

TECHNICAL FIELD

The present invention relates to the use of heat shock protein-90beta (HSP-90beta) as a marker for identifying and/or isolating multipotential cells. More particularly, the invention relates to the identification of a monoclonal antibody (designated STRO-4) which specifically binds human and ovine HSP-90beta. The present invention also relates to cell populations enriched by methods of the present invention and therapeutic uses of these cells.

BACKGROUND OF THE INVENTION

The cellular components that comprise haematopoietic supportive marrow stroma and associated skeletal tissues are derived from a population of multipotential cells including multipotential mesenchymal stem cells (MSC) and their precursors (mesenchymal precursor cells (MPCs)). MPC reside within the bone marrow spaces located primarily in perivascular niches which surround blood vessels (Gronthos S at al., 2003 and Shi S et al., 2003). Over the last two decades, studies have focused on the regenerative potential of different human stromal/mesenchymal cell populations to reconstitute fat, bone, cartilage and muscle (Gronthos S et al., 2003 and Simmons P J at al., 1991). However, the successful application of these technologies is dependent on the ability to isolate purified populations of MPC and to subsequently manipulate their growth and differentiation ex vivo. Moreover, there is a need to overcome the various technical and safety concerns often associated with stem cell based therapies by assessing the safety and efficacy of MPC preparations in appropriate large pre-clinical animal models representative of human diseases. Ovine models of human orthopaedic and cardiac disease/trauma have been widely used, as sheep share similarities with human anatomy, physiology, immunology and embryonic development (Airey J A at al., 2004; Liechty K W at al., 2000 and Mackenzie T C et al., 2001).

Whilst, several human multipotential cell specific markers such as STRO-1, CD106, CD146 have been described in the literature (Gronthos S at al., 2003 and Shi S et al., 2003), significant progress in examining the therapeutic potential of multipotential cells in ovine models of human disease has been limited due a lack of specific reagents which enable the isolation and characterisation of an equivalent multipotential cell population in ovine tissues. The development of biological reagents, such as monoclonal antibodies, reactive with both ovine and human multipotential cells would greatly facilitate the capacity to monitor and equate the functional properties of both ovine and human multipotential cell populations in pre-clinical and clinical trials, respectively.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

The present invention describes the generation and characterisation of a novel monoclonal antibody (mAb), designated STRO-4 that identifies and isolates multipotential cells from unfractionated ovine and human bone marrow. In particular, the STRO-4 antibody is able to isolate essentially all of the clonogenic multipotential cells (CFU-F: colony forming unit fibroblastic) in both species. The isolated multipotential cells exhibit high proliferative potential and multi-lineage differentiation.

Surprisingly, the present inventors have found that the heat shock protein-90 beta (HSP-90beta) protein is expressed on the cell surface of multipotential cells in vivo and monoclonal antibody STRO-4 was found to identify a unique epitope expressed on HSP-90beta.

Accordingly, in one embodiment the present invention provides for the use of HSP-90beta as a marker for the identification and/or enrichment of multipotential cells.

In one embodiment, the present invention provides a method of enriching for multipotential cells, the method comprising preparing a cell sample from a tissue source and enriching for cells that express the HSP-90beta marker.

In one embodiment of the present invention, the multipotential cells are adult multipotential cells.

In one embodiment, the enriched cell population of the invention has not been cultured in vitro.

In another embodiment, the enriched cell population of the invention is capable of giving rise to clonogenic CFU-F.

In another embodiment, the enriched cell population is homogenous for HSP-90beta$^+$/STRO-4$^+$ cells.

In one example, the method of enriching for multipotential cells comprises:
  contacting a cell sample with a HSP-90beta binding agent; and
  separating cells bound to the HSP-90beta binding agent from cells that do not bind the HSP-90beta binding agent.

In another embodiment, the present invention also provides a method for identifying the presence of a multipotential cell in a cell sample, the method comprising identifying cells in sample that express the HSP-90beta marker.

In one example, the method for identifying the presence of a multipotential cell in a cell sample comprises:
  obtaining a cell sample from a tissue source;
  contacting the cell sample with a HSP-90beta binding agent under conditions suitable for binding of HSP-90beta to the HSP-90beta binding agent; and
  detecting the presence of the HSP-90beta binding agent bound to cells in the sample, wherein the presence of multipotential cells is indicated by cells that bind to the HSP-90beta binding agent.

The cell sample may be derived from any tissue source suspected of containing multipotential cells. For example, the tissue source may be placenta, adipose tissue, teeth, dental pulp, skin, liver, kidney, heart, retina, brain, hair follicles, intestine, lung, spleen, lymph node, thymus, ovary, pancreas, bone, ligament, bone marrow, tendon or skeletal muscle. In a preferred embodiment, the tissue source is bone marrow.

The source of cells from which the multipotential cells are enriched may be human or ovine origin. However, the invention is also applicable to cells derived from other animal species, including bovine, equine, murine, porcine, canine, or feline.

The present invention also relates to progeny cells which are produced from the in vitro culture of multipotential cells of the invention. Expanded cells of the invention may have a wide variety of phenotypes depending on the culture conditions (including the number and/or type of stimulatory factors in the culture medium), the number of passages and the like.

In a further embodiment, culturing the enriched population of the invention results in multipotential cells that also express one or more markers selected from the group consisting of STRO-1, STRO-3 (TNSAP), LFA-3, THY-1, VCAM-1, ICAM-1, PECAM-1, P-selectin, L-selectin, CD49a/CD49b/CD29, CD49c/CD29, CD49d/CD29, CD29, CD18, CD61, integrin beta, 6-19, thrombomodulin, CD10, CD13, SCF, PDGF-R, EGF-R, IGF1-R, NGF-R, FGF-R, Leptin-R, (STRO-2=Leptin-R), RANKL, STRO-1$^{bright}$ and CD146 or any combination of these markers.

In another embodiment of the invention, multipotential cells of the invention are not capable of giving rise, upon culturing, to hematopoietic cells.

The methods according to the invention may also include the step of harvesting a source of multipotential cells before the first enrichment step. This may involve, for example, surgically removing tissue from the subject and separating the cells of the tissue to form a single cell suspension. This separation may be achieved by physical or enzymatic means. Such means will be familiar to persons skilled in the art of the present invention. In one example of the invention, this step involves harvesting bone marrow cells using known techniques.

The HSP-90beta binding agent used in the methods of the present invention can be any polypeptide or compound identified as having binding affinity to HSP-90beta.

Preferably, the HSP-90beta binding agent specifically binds to HSP-90beta.

Preferably, the HSP-90beta binding agent specifically binds to an epitope on HSP-90beta wherein HSP-90beta comprises a sequence at least about 75% identical to the sequence of SEQ ID NO:1 (FIG. 5), preferably at least about 78% identical, more preferably at least about 80%, still more preferably at least about 85%, still more preferably at least about 90%, even more preferably at least about 91%, 92%, 93%, 94%, 95%, 96%, 97%, 98%, 99% to SEQ ID NO:1.

In one embodiment, the HSP-90beta binding agent is selected from the group consisting of peptides, peptidomimetics, nucleic acid aptamers, peptide aptamers, dendrimers, and small organic molecules.

In one example, the HSP-90beta binding agent is an oligonucleotide. Preferably, the oligonucleotide is a labelled oligonucleotide.

In another embodiment, the HSP-90beta binding agent is a purified anti-HSP-90beta antibody or antigen binding fragment or derivative thereof. The anti-HSP-90beta antibody may be a monoclonal, recombinant, chimeric, or humanized antibody.

In one embodiment of the present invention, the anti-HSP-90beta monoclonal antibody is the STRO-4 antibody produced by the hybridoma cell line deposited with ATCC on 10 Jul. 2008 under the provisions of the Budapest Treaty under deposit accession number PTA-9362.

Other suitable anti-HSP-90beta monoclonal antibodies for use in the methods of the present invention include commercially available antibodies such as mouse anti-human Hsp90Beta mAb clone H9010 (Invitrogen), mouse anti-Hsp90b mAb clone EMD-5E12 (Calbiochem), mouse anti-human HSP90beta mAb clone K3725B (Cosmo Bio Co., Ltd), and mouse anti-human Hsp90 beta mAb clone K3705 (Assay Designs/Stressgen Bioreagents). Other commercially available antibodies not mentioned above are also considered to be within the scope of the present invention.

In another embodiment, the invention provides an HSP-90beta binding agent or antigen binding fragment or derivative thereof selected from the group consisting of:
(i) a STRO-4 monoclonal antibody;
(ii) a chimeric antibody comprising heavy and light chain variable regions from STRO-4 and human heavy and light chain constant regions; and
(iii) a humanized antibody comprising at least one complementarity determining region (CDR) from STRO-4 and human framework and constant region sequences.

In another embodiment, the humanized antibody comprises all six CDRs from STRO-4.

In another embodiment, the HSP-90beta binding agent is a recombinant antibody comprising a sequence substantially identical to that of the STRO-4 antibody produced by the hybridoma cell line deposited with ATCC on 10 Jul. 2008 under the provisions of the Budapest Treaty under deposit accession number PTA-9362.

In one embodiment of the present invention, the HSP-90beta binding agent is labelled.

On one example, the label is a fluorescent label. In another example, the label is an enzymatic label.

In another embodiment, the separation of cells bound to the HSP-90beta binding agent is carried out by a mechanical cell sorter.

In a further embodiment of the invention, the HSP-90beta binding agent is coupled to a fluorescent labelling compound. In this case, the separation of cells bound to the HSP-90beta binding agent is preferably carried out using a fluorescence-activated cell sorter (FACS).

In a further embodiment of the invention, the HSP-90beta binding agent is linked to a solid particle. Preferably, the solid particle is a magnetic particle. In this embodiment of the invention, the separation of cells bound to the HSP-90beta binding agent is preferably carried out by separating the particulate phase from the liquid phase.

In a further preferred embodiment of the invention, prior to the separation step the cell sample is contacted with an antibody directed against the HSP-90beta binding agent linked to a solid particle, and wherein the separation of cells bound to the HSP-90beta binding agent is carried out by separating the particulate phase from the liquid phase.

In a further embodiment of the invention, the cells of the cell sample are adherent cells cultivated on a solid support, and removal of unbound HSP-90beta binding agent is carried out by rinsing.

In a further embodiment of the invention, the cells of the cell sample are cultivated in suspension, and removal of unbound HSP-90beta binding agent is carried out by centrifuging the cell sample and separating off the resulting supernatant.

In a further embodiment, the cell sample is subjected to a further cell sorting procedure to enrich or diminish the cell population in cells expressing at least one further multipotential cell marker. The multipotential cell marker may one or more markers selected from the group consisting of STRO-1, STRO-3 (TNSAP), CD106, CD146, LFA-3, THY-1, VCAM- 1, ICAM-1, PECAM-1, P-selectin, L-selectin, CD49a/CD49b/CD29, CD49c/CD29, CD49d/CD29, CD29, CD18, CD61, integrin beta, 6-19, thrombomodulin, CD10, CD13, SCF, PDGF-R, EGF-R, IGF1-R, NGF-R, FGF-R, Leptin-R, (STRO-2=Leptin-R), RANKL, or any combination of these markers.

The present invention also provides an enriched population of multipotential cells obtained by a method according to the present invention.

The present invention also provides an enriched population of HSP-90beta+ multipotential cells.

Preferably, at least 1%, 2%, 3%, 4%, 5%, 10%, 15%, 20%, 30%, 40%, 50%, 60%, 70%, 80%, 90% or 95% of the total enriched cell population are multipotential cells that have the phenotype HSP-90beta+.

Preferably, the enriched population of multipotential cells were obtained by a method according to the present invention.

The present invention also provides an expanded cell population obtained by culturing a population of multipotential cells enriched according to the invention.

In one embodiment, the enriched cell population of the invention, or an expanded cell population of the invention, comprises at least some cells which are genetically modified.

The present invention also provides a method of generating a tissue specific committed cell population, the method comprising
culturing a population of multipotential cells of the present invention in the presence of one or more stimulatory factors, and
subjecting said cultured population to conditions biasing differentiation of the multipotential cells to a specific tissue type.

In one embodiment of this method of the invention, the tissue type is selected from the group consisting of placental tissue, cardiac muscle, vascular tissue, bone tissue, cartilage tissue, fat tissue, neural tissue, smooth muscle and endothelial tissue.

The present invention also provides a composition comprising enriched multipotential cells according to the present invention and/or an expanded cell population according to the invention.

In a preferred embodiment, the composition further comprises a stimulatory factor. Such a composition is likely to be beneficial therapeutically and thus will be prepared in a pharmaceutically acceptable form.

In another embodiment the composition further comprises a factor to bias differentiation of the multipotential cells of the present invention to one specific tissue type. Preferably, the tissue type is selected from, but not limited to, the group consisting of cardiac muscle, vascular tissue, bone tissue, cartilage tissue, fat tissue, neural tissue, placental, smooth muscle and endothelial tissue.

In a further embodiment, the composition of the invention further comprises a fibrin glue.

The present invention also provides a method for generating or repairing tissue in a subject, the method comprising administering to the subject an enriched and/or expanded multipotential cell population of the present invention.

The present invention also provides a method for generating or repairing tissue in a subject, the method comprising administering to the subject a composition of the present invention.

The present invention also provides for the use of an enriched and/or expanded multipotential cell population of the present invention for the manufacture of a medicament for generating or repairing tissue in a subject.

Also provided is the use of a composition of the present invention for the manufacture of a medicament for generating or repairing tissue in a subject.

Preferably, the tissue being generated or repaired according to the invention is selected from, but not limited to, the group consisting of cardiac muscle, vascular tissue, bone tissue, cartilage tissue, fat tissue, neural tissue, placental, smooth muscle and endothelial tissue.

Preferably, the multipotential cells according to the invention are of human origin.

The present invention also provides an isolated cell which has been obtained by a method of the invention, or a progeny cell thereof, wherein the cell is genetically modified.

The present invention also provides a STRO-4 hybridoma cell line deposited with ATCC on 10 Jul. 2008 under the provisions of the Budapest Treaty under deposit accession number PTA-9362.

The present invention also provides a STRO-4 antibody produced by the hybridoma cell line deposited with ATCC on 10 Jul. 2008 under the provisions of the Budapest Treaty under deposit accession number PTA-9362.

The present invention also provides an isolated antibody which binds to the same epitope on multipotential cells as the STRO-4 antibody produced by the hybridoma cell line deposited with ATCC on 10 Jul. 2008 under the provisions of the Budapest Treaty under deposit accession number PTA-9362.

The present invention also provides a composition comprising a HSP-90beta binding agent or antigen binding fragment or derivative thereof. Preferably, the composition further comprises one or more pharmaceutically acceptable carriers and/or suitable adjuvants or excipients.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Single colour immunofluorescence and flow cytometry was performed on specimens of Ficoll-separated ovine and human BM MNC to examine the expression of STRO-4 antigen. The mean incidence of STRO-4+ cells in the ovine (A) and human (B) BMMNC samples was 4.0%±1.2 and 3.0%±1.0 (n=3) for each population, respectively. Data are displayed as single-parameter fluorescence (phycoerythrin (PE)) histograms of 1×10$^4$ light-scatter gated events, collected as list mode data. IgG control (dotted line); mAb STRO-3 (solid line). A single cell suspension of unfractionated BM and MACS selected STRO-4+ and STRO-4− ovine (C) and human (D) BMMNC were plated into regular growth medium to assess the incidence of adherent colony-forming cells in each cell fraction. Following 12 days of culture, colonies (aggregates of 50 cells or more) were stained and scored as described in Methods. The bar graph depicts the number of clonogenic colonies per 10$^5$ cells plated for each cell fraction averaged from 3 separate experiments. These data demonstrate that the majority of clonogenic MPC are exclusively restricted to the STRO-4+ fraction of BM.

Figure 2:
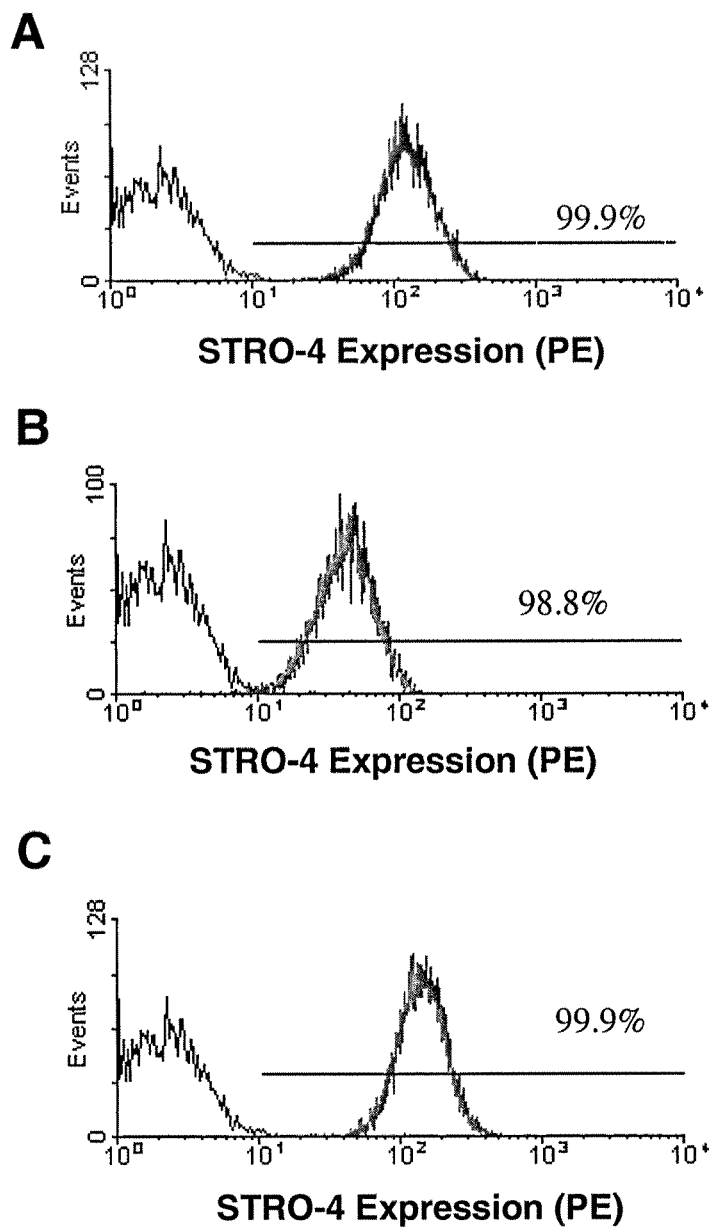

FIG. 2. Ex vivo Expanded MPC Express High levels of the STRO-4 Antigen.

Single cell suspensions of passage two ovine MPC (A) and human MPC (B) and MG63 cells (C) were obtained by trypsin/EDTA digestion then processed for one-colour flow cytometry. The cells were sequentially incubated with STRO-4 supernatant and then indirectly labelled with a goat anti-murine IgG coupled to PE. The histogram represents $2\times10^4$ events collected as listmode data. Positivity (as highlighted by the horizontal statistical marker) for STRO-4 was defined as the level of fluorescence greater than 99% of what was observed when isotype matched, non-binding control antibody (1B5; black line). The results demonstrated that the majority of ex vivo expanded ovine and human MPC expressed STRO-4 (bold line).

Figure 3:
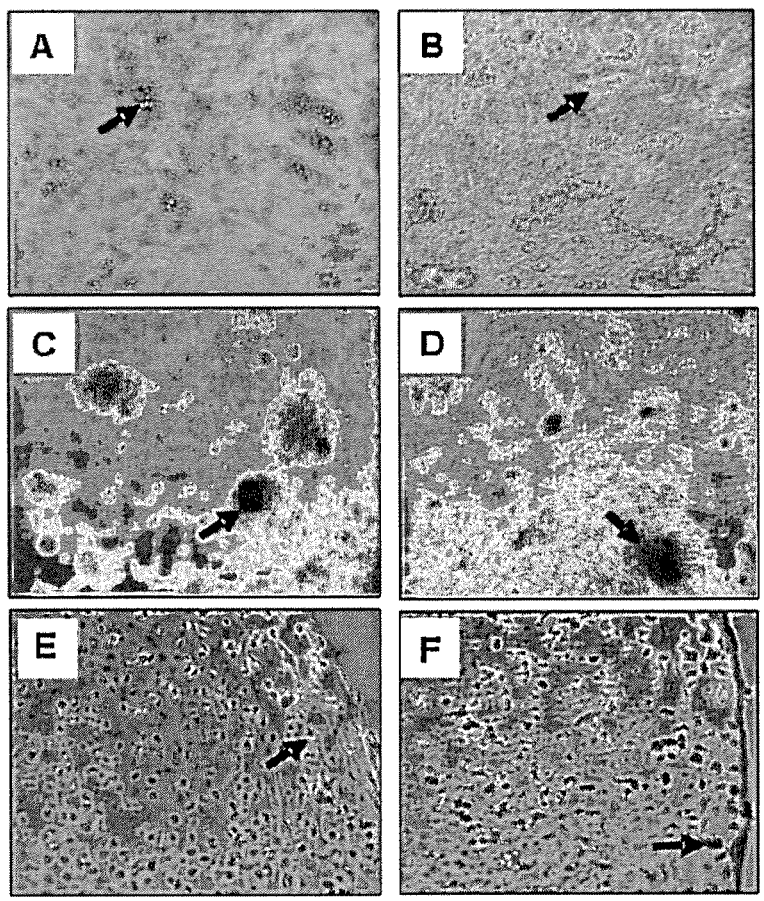

FIG. 3. Developmental potential of STRO-4 Antigen Selected Ovine and Human MPC.

Secondary cultures of cells derived from STRO-4 antigen selected ovine and human MPC were induced under adipocytic, osteogenic, or chondrogenic conditions. The presence of clusters of lipid containing adipocytes were detected by Oil red-O staining (arrow) within 2 weeks of adipogenic induction in the human MPC (A) and ovine MPC (B) cultures (200×). Mineralized deposits stained positively with the Alizarin Red reagent (arrow) formed within 4 weeks of culture under osteoinductive conditions in the human MPC(C) and ovine MPC (D) cultures (200×). In aggregate cultures, Toluidine blue positive staining for proteoglycans was present throughout the cellular mass surrounding chondrocyte-like cells (arrow) following 3 weeks of chondrogenic induction in the human MPC (E) and ovine MPC (F) cultures (arrow) (200×).

Figure 4:
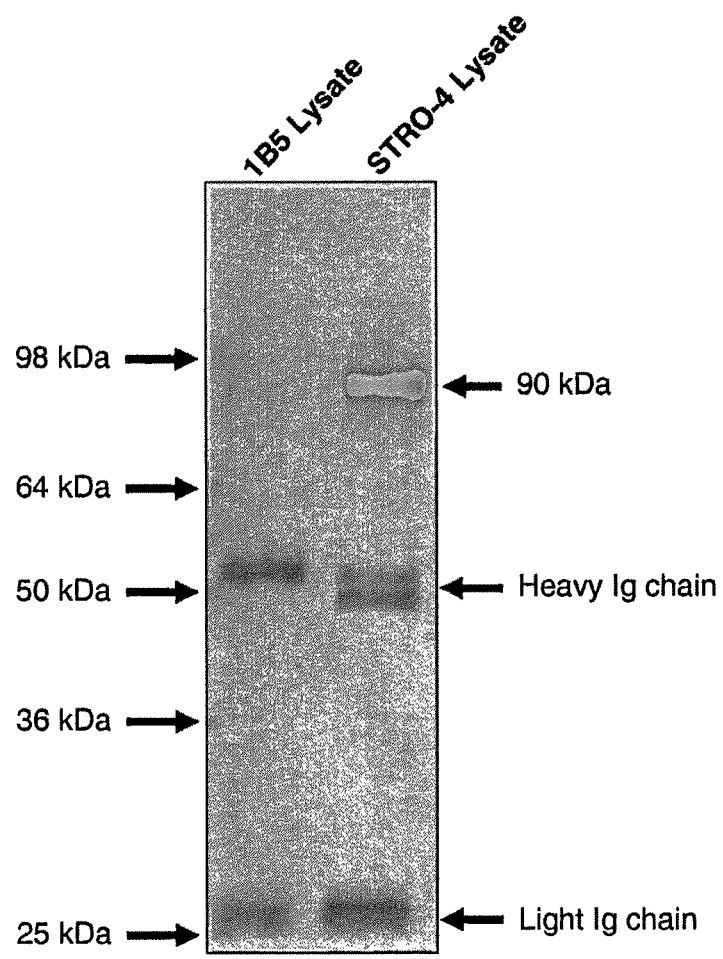

FIG. 4. The STRO-4 Antibody Identifies a 90 kDa Molecular Weight Protein.

Plasma membrane lysates were prepared from single cell suspensions of cultured expanded STRO-4$^+$ human MPC as described in the methods. The cell lysates were incubated with either STRO-4 supernatant or the isotype matched control antibody, 1B5, then immunoprecipitated by magnetic bead separation. The immunoprecipitates were analysed by 10% (w/v) SDS-polyacrylamide gel electrophoresis and visualised following Coomassie blue staining.

FIG. 5. The STRO-4 Antibody Identifies Heat Shock Protein-90 beta.

Plasma membrane lysates were prepared from single cell suspensions of cultured expanded STRO-4$^+$ human MG63 as described in the methods. The cell lysates were incubated with either STRO-4 supernatant then immunoprecipitated by magnetic bead separation. The immunoprecipitates were analysed by 10% (w/v) SDS-polyacrylamide gel electrophoresis and visualised following Coomassie blue staining. The 90 kDa bands were excised from the gels, subjected to Cryptic digestion and analysed by mass spectrometry with an Applied Biosystems 4700 Proteomics Analyser with TOF/TOF optics in MS mode. Microsequencing peptide analysis demonstrated matched (bold) STRO-4 sequenced peptides to human heat shock protein-90 beta (NCBI, accession number, P08238).

Figure 6:
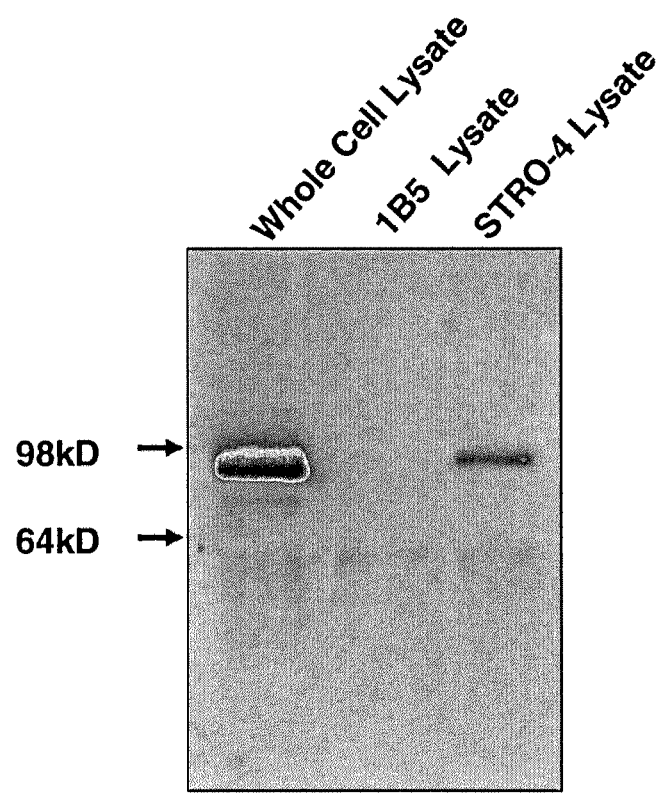

FIG. 6. Confirmation of the Specific Reactivity of the STRO-4 Antibody to Heat Shock Protein-90 beta.

Cultured expanded STRO-4$^+$ human MPC were prepared as whole cell lysates alone or used to generate STRO-4 or 1B5 immunoprecipitates as described in the methods. The whole cell lysates and STRO-4 or 1B5 immunoprecipitates were resolved by electrophoresis on a 10% (w/v) SDS-polyacrylamide gel. Proteins were transferred to PVDF membranes, then blocked with 5% skim milk powder-0.05% Tween-20, before the filters were incubated with a commercially available polyclonal antibody to HSP-90beta. The immunoreactive proteins were visualised using a FluorImager (Molecular Dynamics, Sunnyvale, Calif.) using ImageQuant software (Molecular Dynamics). The anti-HSP-90beta antibody detected a characteristic 90 kDa band in both the control whole cell lysate preparation and in the STRO-4 immunoprecipitate sample.

DETAILED DESCRIPTION OF THE INVENTION

The term "and/or", e.g., "X and/or Y" shall be understood to mean either "X and Y" or "X or Y" and shall be taken to provide explicit support for both meanings or for either meaning.

Micro-Organism Deposit Details

The hybridoma which produces the monoclonal antibody designated STRO-4 was deposited on 10 Jul. 2008 with American Type Culture Collection (ATCC) under accession number PTA-9362.

This deposit was made under the provisions of the Budapest Treaty on the International Recognition of the Deposit of Microorganisms for the Purpose of Patent Procedure and the Regulations thereunder. This assures maintenance of viable cultures for 30 years from the date of deposit. The organisms will be made available by ATCC under the terms of the Budapest Treaty which assures permanent and unrestricted availability of the progeny of the culture to the public upon issuance of the pertinent patent.

The Assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

General Techniques

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and E. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Multipotential Cells

Multipotential cells are cells which are capable of giving rise to any of several mature cell types. In one embodiment the multipotential cells are derived from adult tissue. The term encompasses, for example, mesenchymal precursor cells (MPCs), mesenchymal stem cells (MSC) and multipotential expanded MPC progeny (MEMPs).

Mesenchymal precursor cells (MPCs) are cells found in bone marrow, blood, dermis, and periosteum; and are capable of differentiating into specific types of mesenchymal or connective tissues including adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. Mesenchymal precursor cells are defined as cells which are not terminally differentiated; which can divide without limit; and divide to yield daughter cells that are either stem cells or are progenitor cells which in time will irreversibly differentiate to yield a phenotypically and/or functionally distinct cell type. MPCs are non-hematopoietic progenitor cells that are capable of forming large number of multipotential cells.

Enrichment of Multipotential Cells

The terms 'enriched', 'enrichment' or variations thereof are used herein to describe a population of cells in which the proportion of one particular cell type or the proportion of a number of particular cell types is increased when compared with the untreated population.

The method of enriching for multipotential cells according to the invention may be based on detecting the presence of HSP-90beta marker alone or in combination with one or more additional markers. For example, the method of enriching for multipotential cells may also be based on enriching for cells that are positive for one or more markers selected from the group consisting of STRO-1, STRO-3 (TNSAP), CD106, CD146, LFA-3, THY-1, VCAM-1, ICAM-1, PECAM-1, P-selectin, L-selectin, CD49a/CD49b/CD29, CD49c/CD29, CD49d/CD29, CD29, CD18, CD61, integrin beta, 6-19, thrombomodulin, CD10, CD13, SCF, PDGF-R, EGF-R, IGF1-R, NGF-R, FGF-R, Leptin-R, (STRO-2=Leptin-R), RANKL, or any combination of these markers. Accordingly, an enriched population of multipotential cells of the present invention may also be positive for one or more of these markers or a combination thereof.

Reference to a cell being "positive" for a given marker means it may be either a low (lo or dim) or a high (bright, bri) expresser of that marker depending on the degree to which the marker is present on the cell surface, where the terms relate to intensity of fluorescence or other colour used in the colour sorting process of the cells. The distinction of lo (or dim or dull) and bri will be understood in the context of the marker used on a particular cell population being sorted.

The term "bright", when used herein, refers to a marker on a cell surface that generates a relatively high signal when detectably labelled. Whilst not wishing to be limited by theory, it is proposed that "bright" cells express more of the target marker antigen (for example the antigen recognised by STRO-1) than other cells in the sample. For instance, STRO-1$^{bri}$ cells produce a greater fluorescent signal, when labelled with a fluorescently-conjugated STRO-1 antibody as determined by FACS analysis, than non-bright cells (STRO-1$^{dull/dim}$).

In another example, STRO-1$^{bright}$ cells have 2 log magnitude higher expression of STRO-1 surface expression. This is calculated relative to an isotype matched negative control. By comparison, STRO-1$^{dim}$ and/or STRO-1$^{intermediate}$ cells have less than 2 log magnitude higher expression of STRO-1 surface expression, typically about 1 log or less expression over the isotype matched negative control.

For example, the method may include the step of making a first partially enriched pool of cells by enriching for the expression of a first multipotential cell specific marker, followed by a step of enriching for expression of HSP-90beta from the partially enriched pool of cells. In another example, the method may include an initial enrichment step based on selection of cells expressing HSP-90beta, followed by a step which involves enriching for a different multipotential cell marker. In yet another example, the method involves simultaneously selecting for cells that express HSP-90beta and one or more additional multipotential cell markers.

It is preferred that a significant proportion of the multipotential cells are capable of differentiation into at least two committed cell types. Non-limiting examples of the lineages to which the multipotential cells may differentiate into include, bone precursor cells; hepatocyte progenitors, which are pluripotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells. In a preferred embodiment, the multipotential cells are at least capable of being cultured, in vivo or in vitro, to produce adipocytes, osteoblast and/or chondrocytes.

It will be understood that separation of cells expressing cell surface HSP-90beta can be effected by a number of different methods, however, all of these methods rely at some point upon binding of cells to the HSP-90beta binding agent followed by separation of those cells that exhibit binding, being either high level binding, or low level binding or no binding.

HSP-90beta/STRO-4 Antigen

HSP-90beta is normally present on the cytoplasm of cells where it acts as a molecular chaperone to facilitate the normal folding, intracellular deposition and proteolytic turnover of many key regulators of postnatal cell growth and differentiation. It is part of a highly conserved family of stress response proteins. HSPs are typically expressed at low levels under normal physiological conditions but show dramatically increased expression in response to cellular stress.

It is to be understood that the term "HSP-90beta" is not limited to the sequence of human or ovine origin but also includes homologous sequences obtained from any source, for example homologues, particularly orthologues (i.e. homologues obtained from species other than humans), allelic variants, as well as fragments and synthetic peptides or derivatives thereof.

The sequence identity (% identity) of a polypeptide is determined by FASTA (Pearson and Lipman, (1988)) analysis (GCG program) using the default settings and a query sequence of at least 50 amino acids in length, and whereby the FASTA analysis aligns the two sequences over a region of at least 50 amino acids. More preferably, the FASTA analysis aligns the two sequences over a region of at least 100 amino acids. More preferably, the FASTA analysis aligns the two sequences over a region of at least 250 amino acids. Even more preferably, the FASTA analysis aligns the two sequences over a region of at least 350 amino acids.

The term "HSP-90beta" also encompasses fragments of the above mentioned full-length polypeptides and variants thereof, including fragments of the HSP-90beta sequence.

Preferred fragments include those that include an epitope. Suitable fragments will be at least about 6 or 7 amino acids in length, e.g. at least 10, 12, 15 or 20 amino acids in length. They may also be less than 200, 100 or 50 amino acids in length.

HSP-90beta Binding Agents

When used herein, the phrase "HSP-90beta binding agent" refers to a moiety that recognises and/or specifically binds to HSP-90beta.

By "binds specifically to" it is meant that the HSP-90beta binding agent is capable of binding to HSP-90beta with suitable affinity and/or avidity so as to provide a useful tool for selective enrichment of cells expressing HSP-90beta. That is, it associates more frequently, more rapidly, with greater duration and/or with greater affinity with HSP-90beta than it does with alternative targets (e.g. non-HSP-90beta). For example, an HSP90beta binding agent that specifically binds to HSP90beta or an epitope or immunogenic fragment thereof binds with greater affinity, avidity, more readily, and/or with greater duration than it binds to other non-HSP90beta targets.

Preferred HSP-90beta binding agents are polypeptides or compounds identified as having binding affinity to HSP-90beta.

Non-Antibody Based Binding Agents

The HSP-90beta binding agent of the invention includes peptides, petidomimetics, nucleic acid aptamers, peptide aptamers, dendrimers and small organic molecules.

A nucleic acid aptamer (adaptable oligomer) is a nucleic acid molecule that is capable of forming a secondary and/or tertiary structure that provides the ability to bind to a molecular target. An aptamer library is produced, for example, by cloning random oligonucleotides into a vector (or an expression vector in the case of an RNA aptamer), wherein the random sequence is flanked by known sequences that provide the site of binding for PCR primers. An aptamer with increased activity is selected, for example, using SELEX (Sytematic Evolution of Ligands by EXponential enrichment). Suitable methods for producing and/or screening an aptamer library are described, for example, in Elloington and Szostak, Nature 346:818-22, 1990.

Techniques for synthesizing small organic compounds will vary considerably depending upon the compound, however such methods will be well known to those skilled in the art. In one embodiment, informatics is used to select suitable chemical building blocks from known compounds, for producing a combinatorial library. For example, QSAR (Quantitative Structure Activity Relationship) modelling approach uses linear regressions or regression trees of compound structures to determine suitability. The software of the Chemical Computing Group, Inc. (Montreal, Canada) uses high-throughput screening experimental data on active as well as inactive compounds, to create a probabilistic QSAR model, which is subsequently used to select lead compounds. The Binary QSAR method is based upon three characteristic properties of compounds that form a "descriptor" of the likelihood that a particular compound will or will not perform a required function: partial charge, molar refractivity (bonding interactions), and log P (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, lead compounds identified in initial screens, can be used to expand the list of compounds being screened to thereby identify highly active compounds.

Antibody Based Binding Agents

Particularly preferred HSP-90beta binding agents are anti-HSP-90beta antibodies or antigen binding fragments thereof or derivatives/variants thereof (naturally occurring or recombinant, from any source).

As used herein, the term "antibody" refers to an immunoglobulin molecule capable of binding to a target, such as HSP-90beta and/or an epitope thereof and/or an immunogenic fragment thereof and/or a modified form thereof (e.g., glycosylated, glycosylated, etc.) through at least one epitope recognition site, located in the variable region of the immunoglobulin molecule. This term encompasses not only intact polyclonal or monoclonal antibodies, but also variants, fusion proteins comprising an antibody portion with an epitope recognition site of the required specificity, humanized antibodies, human antibodies, chimeric antibodies, and any other modified configuration of the immunoglobulin molecule that comprises an epitope recognition site of the required specificity.

The term "antibody binding fragment" as used herein shall be taken to mean any fragment of an antibody that retains the ability to bind to HSP-90beta, preferably specifically to HSP-90beta. This includes:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab)$_2$, the fragment of the antibody that can be obtained by treating whole antibody with the enzyme pepsin without subsequent reduction; F(ab)$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

(6) Single domain antibody, preferably a variable heavy domain devoid of light chain.

Methods of making these fragments are known in the art. (See for example, Harlow and Lane, Antibodies: A Laboratory Manual, Cold Spring Harbour Laboratory, New York (1988), incorporated herein by reference).

The term "monoclonal antibody" refers to a homogeneous antibody population capable of binding to the same antigen(s) and, preferably, to the same epitopic determinant within the antigen(s). This term is not intended to be limited as regards to the source of the antibody or the manner in which it is made.

The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass, as well as fragments of such antibodies, so long as they exhibit the desired biological activity (U.S. Pat. No. 4,816,567; and Morrison et al. (1984) *Proc. Natl. Acad. Sci USA* 81:6851-6855).

The term "humanized antibody" shall be understood to refer to a chimeric molecule, generally prepared using recombinant techniques, having an epitope binding site derived from an immunoglobulin from a non-human species and the remaining immunoglobulin structure of the molecule based upon the structure and/or sequence of a human immunoglobulin. The antigen-binding site preferably comprises the complementarity determining regions (CDRs) from the non-human antibody grafted onto appropriate framework regions in the variable domains of human antibodies and the remaining regions from a human antibody. Epitope binding sites may be wild type or modified by one or more amino acid substitutions. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach is known in the art and/or described in more detail herein.

The term constant region (CR) as used herein, refers to the portion of the antibody molecule which confers effector functions. The constant regions of the subject humanized antibodies are derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Preferred heavy chain constant regions are gamma 1 (IgG1), gamma 2 (IgG2), gamma 3 (IgG3) and gamma 4 (IgG4). Light chain constant regions can be of the kappa or lambda type, preferably of the kappa type.

"Framework regions" are those variable domain residues other than the CDR residues. Each variable domain of a naturally-occurring antibody typically has four FRs identified as FR1, FR2, FR3 and FR4. If the CDRs are defined according to Kabat, the light chain FR residues are positioned at about residues 1-23 (LCFR1), 35-49 or 40-54 (LCFR2), 57-88 or 62-93 (LCFR3), and 98-107 or 103-112 (LCFR4) and the heavy chain FR residues are positioned about at about residues 1-30 or 1-30 (HCFR1), 36-49 (HCFR2), 66-94 or 67-96 (HCFR3), and 103-113 or 109-119 (HCFR4) in the heavy chain residues. If the CDRs comprise amino acid residues from hypervariable loops, the light chain FR residues are positioned about at about residues 1-25 (LCFR1), 33-49 (LCFR2), 53-90 (LCFR3), and 97-107 (LCFR4) in the light chain and the heavy chain FR residues are positioned about at about residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. The skilled artisan will be aware of some variation in the positioning of the FRs, e.g., as a result of mutations (e.g., deletions and/or insertions), e.g., up to 5 residues variation, or 4 residues variation, or 2 residues variation, or 1 residue variation (e.g., as exemplified antibodies herein).

As used herein, the term "complementarity determining regions" (syn. CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 or 24-39 (L1)), 50-56 or 55-61 (L2) and 89-97 or 93-102 (L3) in the light chain variable domain and 31-35 or 26-35 (H1), 50-65 or 50-66 (H2) and 95-102 or 97-108 (H3) in the heavy chain variable domain; Kabat et al., Sequences of Proteins of Immunological Interest, 5th Ed, Public Health Service, National Institutes of Health, Bethesda, Md. (1991)) and/or those residues from a "hypervariable loop" i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) *J. Mol. Biol.* 196:901-917). In some instances, a complementarity determining region can include amino acids from both a CDR region defined according to Kabat and a hypervariable loop. The skilled artisan will be aware of some variation in the positioning of the FRs, e.g., as a result of mutations (e.g., deletions and/or insertions), e.g., up to 5 residues variation, or 4 residues variation, or 2 residues variation, or 1 residue variation (e.g., as exemplified antibodies herein).

The term "derivative" as used herein in intended to refer to an anti-HSP-90beta antibody or antigen binding fragment thereof comprising one or more conservative amino acid substitutions. The term "conservative substitution" shall be taken to mean amino acid substitutions set forth in Table 1.

TABLE 1

Exemplary Substitutions

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

The term "conservative substitution" also encompasses substitutions of amino acids having a similar hydropathic index or score. Each amino acid has been assigned a hydropathic index on the basis of their hydrophobicity and charge characteristics, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making changes based upon the hydropathic index, the substitution of amino acids whose hydropathic indices are within +/−0.2 is preferred. More preferably, the substitution will involve amino acids having hydropathic indices within +/−0.1, and more preferably within about +/−0.05.

The term "conservative amino acid substitution" also encompasses substitution of like amino acids made on the basis of hydrophilicity, particularly where the biological functional equivalent protein or peptide thereby created is intended for use in immunological embodiments, as in the present case. For example, the greatest local average hydrophilicity of a protein, as governed by the hydrophilicity of its adjacent amino acids, correlates with its immunogenicity and antigenicity. As detailed in U.S. Pat. No. 4,554,101, the following hydrophilicity values have been assigned to amino acid residues: arginine (+3.0); lysine (+3.0); aspartate (+3.0+/−0.1); glutamate (+3.0+/−0.1); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is preferred to substitute amino acids having hydrophilicity values within about +/−0.2 of each other, more preferably within about +/−0.1, and even more preferably within about +/−0.05

The term "derivative" in relation to the amino acid sequences of the present invention and/or for use in the present invention includes any substitution of, variation of, modification of, replacement of, deletion of or addition of one (or more) amino acids from or to the sequence providing the resultant amino acid sequence preferably has at least 50% of the biological activity as a naturally occurring HSP-90beta more preferably at least substantially the same activity.

The term "derivative" as used herein also comprises an additional component directly or indirectly linked to the antibody or antigen-binding fragment. For example, the derivative comprises a compound that enhances or increases the half life of the antibody in vivo, e.g., polyethylene glycol or albumin. In another example, the derivative additionally comprises a detectable compound, e.g., a fluorescent compound or a radioactive compound or an enzyme, e.g., to facilitate detection and/or imaging. In a further example, the derivative additionally comprises a toxic compound, e.g., a radioactive compound or a cellular toxin.

Methods of recombinantly producing antibodies will be familiar to persons skilled in the art of the present invention. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991).

Antibodies of the present invention can be prepared using cells expressing full length HSP-90beta or fragments thereof as the immunizing antigen. A peptide used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide may then be used to immunize the animal (e.g., a mouse or a rabbit).

If desired, polyclonal antibodies can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

Monoclonal antibodies may be prepared using any technique which provides for the production of antibody molecules by continuous cell lines in culture, such as, for example, the hybridoma technique, the human B-cell hybridoma technique, and the EBV-hybridoma technique (Kohler et al., 1975; Kozbor et al., 1985; Cote et al., 1983; Cole et al., 1984).

Methods known in the art also allow antibodies exhibiting binding for HSP-90beta to be identified and isolated from antibody expression libraries.

Antibodies with an epitopic specificity which is the same as or similar to that of mAb STRO-4 can be identified by their ability to compete with that particular mAb for binding to HSP-90beta (e.g. to cells bearing HSP-90beta, such as MPCs, or to isolated HSP-90 protein or fragments thereof). Using receptor chimeras (Rucker et al., 1996) or other techniques known to those skilled in the art, the binding site of STRO-4 mAb may be mapped.

It is also possible to determine, without undue experimentation, if a monoclonal antibody has the same specificity as STRO-4 mAb by ascertaining whether the former prevents the latter from binding to HSP-90beta. If the monoclonal antibody being tested competes with STRO-4 mAb, as shown by a decrease in binding by STRO-4 mAb, then the two monoclonal antibodies bind to the same, or a closely related, epitope.

Still another way to determine whether a monoclonal antibody has the specificity of STRO-4 mAb is to pre-incubate the monoclonal antibody being tested with HSP-90beta, and then add STRO-4 mAb to determine if STRO-4 mAb is inhibited in its ability to bind to HSP-90beta. If the binding of STRO-4 mAb is inhibited then, in all likelihood, the monoclonal antibody being tested has the same, or functionally equivalent, epitopic specificity as STRO-4 mAb.

Monoclonal antibodies useful in the present invention can be engineered so as to change the isotype of the antibody. For example, an IgG2A isotype can be engineered as an IgG1, IgG2B, or other isotypes.

It will be appreciated that a HSP-90beta binding agent such as an antibody of the invention may be conjugated to a compound that is useful, for example, in cell separation, therapeutic or diagnostic applications. In one example, an antibody of the invention is conjugated to a label. The label may be any entity the presence of which can be readily detected. For example, the label may be a direct label, such as those described in detail in May et al., U.S. Pat. No. 5,656,503. Direct labels are not limited to but include entities which, in their natural state, are readily visible either to the naked eye, or with the aid of an optical filter and/or applied stimulation, e.g. UV light to promote fluorescence. Examples include radioactive, chemiluminescent, electroactive (such as redox labels), and fluorescent compounds. Direct particulate labels, such as dye sols, metallic sols (e.g. gold) and coloured latex particles, are also very suitable and are, along with fluorescent compounds, preferred. Of these options, coloured latex particles and fluorescent compounds are most preferred. Concentration of the label into a small zone or volume should give rise to a readily detectable signal, e.g. a strongly coloured area. Indirect labels, such as enzymes, e.g. alkaline phosphatase and horseradish peroxidase, can also be used, although these usually require the addition of one or more developing reagents such as substrates before a visible signal can be detected.

Conjugation of a label to a binding agent such as an antibody of the invention can be by covalent or non-covalent (including hydrophobic) bonding, or by adsorption. Techniques for such conjugation are commonplace in the art and may be readily adapted for the particular reagents employed.

A binding agent for use in the methods of the invention, such as an antibody of the invention, may also be coated onto a solid support. For example, the antibody can be coated on a synthetic plastics material, magnetic particle, microtitre assay plate, microarray chip, latex bead, filter comprising a cellulosic or synthetic polymeric material, glass or plastic slide, dipstick, capillary fill device and the like.

The HSP-90beta binding agent may be attached to a solid support to allow for a crude separation. The separation techniques preferably maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to MACS, Dynal magnetic bead selection and FACS.

Cell Sorting Techniques

The ability to recognise mesenchymal precursor cells with HSP-90beta binding agents, such as anti-HSP-90beta antibodies, allows not only for the identification and quantification of these cells in tissue samples, but also for their separation and enrichment in suspension. This can be achieved by a number of cell-sorting techniques by which cells are physically separated by reference to a property associated with the cell-antibody complex, or a label attached to the antibody. This label may be a magnetic particle or a fluorescent molecule. The antibodies may be cross-linked such that they form aggregates of multiple cells, which are separable by their density. Alternatively the antibodies may be attached to a stationary matrix, to which the desired cells adhere.

Various methods of separating antibody-bound cells from unbound cells are known. For example, the antibody bound to the cell (or an anti-isotype antibody) can be labelled and then the cells separated by a mechanical cell sorter that detects the presence of the label. Fluorescence-activated cell sorters are well known in the art.

In one embodiment, the anti-HSP-90beta antibody is attached to a solid support. Various solid supports are known to those of skill in the art, including, but not limited to, agarose beads, polystyrene beads, hollow fiber membranes, polymers, and plastic petri dishes. Cells that are bound by the antibody can be removed from the cell suspension by simply physically separating the solid support from the cell suspension.

Super paramagnetic microparticles may be used for cell separations. For example, the microparticles may be coated with anti-HSP-90beta antibodies. The antibody-tagged, super paramagnetic microparticles may then be incubated with a solution containing the cells of interest. The microparticles bind to the surfaces of the desired multipotential cells, and these cells can then be collected in a magnetic field.

In another example, the cell sample is allowed to physically contact, for example, a solid phase-linked anti-HSP-90beta monoclonal antibody. The solid-phase linking can comprise, for instance, adsorbing the antibodies to a plastic, nitrocellulose, or other surface. The antibodies can also be adsorbed on to the walls of the large pores (sufficiently large to permit flow-through of cells) of a hollow fiber membrane. Alternatively, the antibodies can be covalently linked to a surface or bead, such as Pharmacia Sepharose 6 MB macrobeads. The exact conditions and duration of incubation for the solid phase-linked antibodies with the multipotential cell containing suspension will depend upon several factors specific to the system employed. The selection of appropriate conditions, however, is well within the skill of the art.

The unbound cells are then eluted or washed away with physiologic buffer after allowing sufficient time for the multipotential cells to be bound. The unbound cells can be recovered and used for other purposes or discarded after appropriate testing has been done to ensure that the desired separation had been achieved. The bound cells are then separated from the solid phase by any appropriate method, depending mainly upon the nature of the solid phase and the antibody. For example, bound cells can be eluted from a plastic petri dish by vigorous agitation. Alternatively, bound cells can be eluted by enzymatically "nicking" or digesting an enzyme-sensitive "spacer" sequence between the solid phase and the antibody. Spacers bound to agarose beads are commercially available from, for example, Pharmacia.

The eluted, enriched fraction of cells may then be washed with a buffer by centrifugation and either said enriched fraction or the unbound fraction may be cryopreserved in a viable state for later use according to conventional technology or introduced into the transplant recipient.

Differentiation of Multipotential Cells

Conditions that bias differentiation of the multipotential cells of the present invention to bone precursor cells or bone may involve, for example, culturing in αMEM supplemented with 10% FCS, 100 μM L-ascorbate-2-phosphate, dexamethasone $10^{-7}$ M and 3 mM inorganic phosphate. These conditions have been shown to induce human bone marrow stromal cells to develop a mineralized bone matrix in vitro (Gronthos et al., 1994).

Suitable conditions for differentiating the multipotential cells of the present invention into osteoblasts may involve cultivating the cells in the presence of type I collagen, fibrinogen, fibrin, polyglycolic acid, polylactic acid, osteocalcin, or osteonectin. In one particular example, the cells are cultivated in the presence of type I collagen, fibrinogen, and fibrin. In an alternative example, the cells are cultivated in the presence of type I collagen, fibrinogen, fibrin, osteocalcin, and osteonectin. In the context of this method, type I collagen, fibrinogen, fibrin, polyglycolic acid, polylactic acid, osteocalcin, or osteonectin may be used alone or in the presence of a growth factor. It will be understood that any combination of the compounds listed above in this paragraph is contemplated by the present invention.

Production of Genetically Modified Cells

In one embodiment the present invention relates to genetically modified cells, particularly genetically modified multipotential cells of the invention. Preferably, the cells are genetically modified to produce a heterologous protein. Typically, the cells will be genetically modified such that the heterologous protein is secreted from the cells. The heterologous protein may be any protein of interest. For example, the heterologous protein may be platelet derived growth factor (PDGF), tumor necrosis factor α (TNF-α), interleukin-1β (IL-1β) and stromal derived factor 1α (SDF-1α).

In another example, the heterologous protein is a bioactive factor which accelerates differentiation of the multipotential cells to specific tissue types. The bioactive factor may be, for example, a synthetic glucocorticoid, or a bone morphogenic protein, such as BMP-2, BMP-3, BMP-4, BMP-6 or BMP-7.

In an embodiment the cells can be modified to express a functional non-protein encoding polynucleotide such as dsRNA (typically for RNA silencing), an antisense oligonucleotide or a catalytic nucleic acid (such as a ribozyme or DNAzyme).

Genetically modified cells may be cultured in the presence of at least one cytokine in an amount sufficient to support growth of the modified cells. The genetically modified cells thus obtained may be used immediately (e.g., in transplant), cultured and expanded in vitro, or stored for later uses. The modified cells may be stored by methods well known in the art, e.g., frozen in liquid nitrogen.

Genetic modification as used herein encompasses any genetic modification method which involves introduction of an exogenous or foreign polynucleotide into an multipotential cell or modification of an endogenous gene within multipotential cells. Genetic modification includes but is not limited to transduction (viral mediated transfer of host DNA from a host or donor to a recipient, either in vitro or in vivo), transfection (transformation of cells with isolated viral DNA genomes), liposome mediated transfer, electroporation, calcium phosphate transfection or coprecipitation and others. Methods of transduction include direct co-culture of cells with producer cells (Bregni et al., 1992) or culturing with viral supernatant alone with or without appropriate growth factors and polycations (Xu et al., 1994).

An exogenous polynucleotide is preferably introduced to a host cell in a vector. The vector preferably includes the necessary elements for the transcription and translation of the inserted coding sequence. Methods used to construct such vectors are well known in the art. For example, techniques for constructing suitable expression vectors are described in detail in Sambrook et al., Molecular Cloning: A Laboratory Manual, Cold Spring Harbor Press, N.Y. (3rd Ed., 2000); and Ausubel et al., Current Protocols in Molecular Biology, John Wiley & Sons, Inc., New York (1999).

Vectors may include but are not limited to viral vectors, such as retroviruses, adenoviruses, adeno-associated viruses, and herpes simplex viruses; cosmids; plasmid vectors; synthetic vectors; and other recombination vehicles typically used in the art. Vectors containing both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). Specific examples include, pSG, pSV2CAT, pXt1 from Stratagene; and pMSG, pSVL, pBPV and pSVK3 from Pharmacia.

Preferred vectors include retroviral vectors (see, Coffin et al., "Retroviruses", Chapter 9 pp; 437-473, Cold Springs Harbor Laboratory Press, 1997). Vectors useful in the invention can be produced recombinantly by procedures well known in the art. For example, WO94/29438, WO97/21824 and WO97/21825 describe the construction of retroviral packaging plasmids and packing cell lines. Exemplary vectors include the pCMV mammalian expression vectors, such as pCMV6b and pCMV6c (Chiron Corp.), pSFFV-Neo, and pBluescript-Sk+. Non-limiting examples of useful retroviral vectors are those derived from murine, avian or primate retroviruses. Common retroviral vectors include those based on the Moloney murine leukemia virus (MoMLV-vector). Other MoMLV derived vectors include, Lmily, LINGFER, MINGFR and MINT. Additional vectors include those based on Gibbon ape leukemia virus (GALV) and Moloney murine sarcoma virus (MOMSV) and spleen focus forming virus (SFFV). Vectors derived from the murine stem cell virus (MESV) include MESV-MiLy. Retroviral vectors also include vectors based on lentiviruses, and non-limiting examples include vectors based on human immunodeficiency virus (HIV-1 and HIV-2).

In producing retroviral vector constructs, the viral gag, pol and env sequences can be removed from the virus, creating room for insertion of foreign DNA sequences. Genes encoded by foreign DNA are usually expressed under the control a strong viral promoter in the long terminal repeat (LTR). Selection of appropriate control regulatory sequences is dependent on the host cell used and selection is within the skill of one in the art. Numerous promoters are known in addition to the promoter of the LTR. Non-limiting examples include the phage lambda PL promoter, the human cytomegalovirus (CMV) immediate early promoter; the U3 region promoter of the Moloney Murine Sarcoma Virus (MMSV), Rous Sacroma Virus (RSV), or Spleen Focus Forming Virus (SFFV); Granzyme A promoter; and the Granzyme B promoter. Additionally inducible or multiple control elements may be used. The selection of a suitable promoter will be apparent to those skilled in the art.

Such a construct can be packed into viral particles efficiently if the gag, pol and env functions are provided in trans by a packing cell line. Therefore, when the vector construct is introduced into the packaging cell, the gag-pol and env proteins produced by the cell, assemble with the vector RNA to produce infectious virons that are secreted into the culture medium. The virus thus produced can infect and integrate into the DNA of the target cell, but does not produce infectious viral particles since it is lacking essential packaging sequences. Most of the packing cell lines currently in use have been transfected with separate plasmids, each containing one of the necessary coding sequences, so that multiple recombination events are necessary before a replication competent virus can be produced. Alternatively the packaging cell line harbours a provirus. The provirus has been crippled so that although it may produce all the proteins required to assemble infectious viruses, its own RNA cannot be packaged into virus. RNA produced from the recombinant virus is packaged instead. Therefore, the virus stock released from the packaging cells contains only recombinant virus. Non-limiting examples of retroviral packaging lines include PA12, PA317, PE501, PG13, PSLCRIP, RDI 14, GP7C-tTA-G10, ProPak-A (PPA-6), and PT67. Reference is made to Miller et al., 1986; Danos et al., 1988; Pear et al., 1993; and Finer et al., 1994.

Other suitable vectors include adenoviral vectors (see, Frey et al., 1998; and WO 95/27071) and adeno-associated viral vectors. These vectors are all well known in the art, e.g., as described in Chatterjee et al., 1996; and Stem Cell Biology and Gene Therapy, eds. Quesenberry et al., John Wiley & Sons, 1998; and U.S. Pat. Nos. 5,693,531 and 5,691,176. The use of adenovirus-derived vectors may be advantageous under certain situation because they are not capable of infecting non-dividing cells. Unlike retroviral DNA, the adenoviral DNA is not integrated into the genome of the target cell. Further, the capacity to carry foreign DNA is much larger in adenoviral vectors than retroviral vectors. The adeno-associated viral vectors are another useful delivery system. The DNA of this virus may be integrated into non-dividing cells, and a number of polynucleotides have been successful introduced into different cell types using adeno-associated viral vectors.

In some embodiments, the construct or vector will include two or more heterologous polynucleotide sequences. Preferably the additional nucleic acid sequence is a polynucleotide which encodes a selective marker, a structural gene, a therapeutic gene, or a cytokine/chemokine gene.

A selective marker may be included in the construct or vector for the purposes of monitoring successful genetic modification and for selection of cells into which DNA has been integrated. Non-limiting examples include drug resistance markers, such as G418 (neomycin sulphate) or hygromycin. Additionally negative selection may be used, for example wherein the marker is the HSV-tk gene. This gene will make the cells sensitive to agents such as acyclovir and gancyclovir. The NeoR (neomycin/G418 resistance) gene is commonly used but any convenient marker gene may be used whose gene sequences are not already present in the target cell can be used. Further non-limiting examples include low-affinity Nerve Growth Factor (NGFR), enhanced fluorescent green protein (EFGP), dihydrofolate reductase gene (DHFR) the bacterial hisD gene, murine CD24 (HSA), murine CD8a (lyt), bacterial genes which confer resistance to puromycin or phleomycin, and β-glactosidase.

The additional polynucleotide sequence(s) may be introduced into the host cell on the same vector or may be introduced into the host cells on a second vector. In a preferred embodiment, a selective marker will be included on the same vector as the polynucleotide.

The present invention also encompasses genetically modifying the promoter region of an endogenous gene such that expression of the endogenous gene is up-regulated resulting in the increased production of the encoded protein compared to wild type multipotential cells.

Use of Enriched Multipotential Cell Compositions

Enrichment of multipotential cells such as MPCs is desirable for a variety of therapeutic purposes. These include regeneration of missing or damaged skeletal tissue, enhancing the implantation of various plastic or metal prosthetic devices through the attachment of the isolated or culturally expanded marrow derived mesenchymal cells onto the porous surfaces of the prosthetic devices, which upon activation and subsequent differentiation of marrow-derived mesenchymal cells produce natural osseous bridges.

Composite grafts of cultured mesenchymal cells might be used to augment the rate of haematopoietic cell reserve during bone marrow transplantation.

A class of defect that may be repaired by cultured marrow-derived mesenchymal cells expanded from the multipotential cells of the present invention is the class of large skeletal defects in bone caused by injury or produced by the removal of large sections of bone infected with tumour. Under normal circumstances this type of defect does not heal and creates non-union of the bone. This type of defect may be treated by implanting cultured mesenchymal cells contained in calcium phosphate ceramic vehicles into the defect site.

Another class of defect that may be repaired by cultured marrow-derived mesenchymal cells expanded from the multipotential cells of the present invention is the damaged articular cartilage generated by trauma or by diseases such as osteoarthritis and rheumatoid arthritis.

The enriched or expanded cell population of multipotential cells obtained according to the present invention may be used, for example, in the formation and repair of bones, and as such a combination of multipotential cells as well as a suitable support may be introduced into a site requiring bone formation. Thus, for example, skeletal defects caused by bone injury or the removal of sections of bone infiltrated with tumour may be repaired by implanting cultured or expanded multipotential cells contained in calcium phosphate ceramic vehicles into the defect site. For appropriate methods and techniques see Caplan et al., in U.S. Pat. No. 5,226,914 and U.S. Pat. No. 5,837,539, both of which use cruder preparations of stem cells when compared to the present invention.

In addition, the enriched cell population or composition may be used to assist in anchoring prosthetic devices. Thus, the surface of a prosthetic device such as those used in hip, knee and shoulder replacement, may be coated with the enriched multipotential cells prior to implantation. The multipotential cells may then differentiate into osteogenic cells to thereby speed up the process of bony ingrowth and incorporation of the prosthetic device (see Caplan et al., in U.S. Pat. No. 5,226,914 and U.S. Pat. No. 5,837,539).

The enriched cell population or composition might also be used in gene therapy so that, for example, an enriched population may have exogenous nucleic acid transformed into it and then such a population may be introduced into the body of the patient to treat a disease or condition. Alternatively it might be used for the release of therapeutics. For appropriate techniques we refer to U.S. Pat. No. 5,591,625 by Gerson et al. which uses cruder preparations of stem cells when compared to the present invention.

Alternatively the enriched population or composition may be used to augment bone marrow transplantation, wherein the composition containing enriched multipotential cells can be injected into a patient undergoing marrow transplantation prior to the introduction of the whole marrow. In this way the rate of haemopoiesis may be increased, particularly following radiation or chemotherapy. The composition might also encompass a mixture of multipotential cells and haemopoietic cells which may be useful in radiotherapy or chemotherapy.

Cellular Compositions

The cellular compositions of the present invention, such as those comprising multipotential cells such as MPCs, are useful for the regeneration of tissue of various types, including bone, cartilage, tendon, ligament, muscle, skin, and other connective tissue, as well as nerve, cardiac, liver, lung, kidney, pancreas, brain, and other organ tissues.

As used herein "pharmaceutically acceptable carrier" or "excipient" including, but not limited to any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In some embodiments, the compositions of the present invention may be administered in combination with an appropriate matrix, for instance, for supporting the cells and providing a surface for bone, cartilage, muscle, nerve, epidermis and/or other connective tissue growth. The matrix may be in the form of traditional matrix biomaterials. The matrix may provide slow release of cells and/or the appropriate environment for presentation thereof. In some embodiments, various collagenous and non-collagenous proteins are expected to be upregulated and secreted from the cells. This phenomenon accelerates tissue regeneration by enhancing matrix deposition. Matrix proteins can also be expressed in the genetically engineered cells and enhance the engraftment and attachment of transplanted cells into the transplant area.

The cellular compositions of the invention may be administered alone or as admixtures with other cells. Cells that may be administered in conjunction with the compositions of the present invention include, but are not limited to, other multipotent or pluripotent cells or chondrocytes, chondroblasts, osteocytes, osteoblasts, osteoclasts, bone lining cells, stem cells, or bone marrow cells. The cells of different types may be admixed with a composition of the invention immediately or shortly prior to administration, or they may be co-cultured together for a period of time prior to administration.

The cellular compositions of the invention may be administered with other beneficial drugs or biological molecules (growth factors, trophic factors). When the multipotential cells are administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics. As another example, the cells may be co-administered with scar inhibitory factor as described in U.S. Pat. No. 5,827,735, incorporated herein by reference.

In one embodiment, cellular compositions of the invention are administered as undifferentiated cells, i.e., as cultured in Growth Medium. Alternatively, the cellular compositions may be administered following exposure in culture to conditions that stimulate differentiation toward a desired phenotype, for example, an osteogenic phenotype.

Fibrin Glue

Fibrin glues are a class of surgical sealants which have been used in various clinical settings. As the skilled address would be aware, numerous sealants are useful in compositions of the invention. However, a preferred embodiment of the invention relates to the use of fibrin glues with cells of the invention.

When used herein the term "fibrin glue" refers to the insoluble matrix formed by the cross-linking of fibrin polymers in the presence of calcium ions. The fibrin glue may be formed from fibrinogen, or a derivative or metabolite thereof, fibrin (soluble monomers or polymers) and/or complexes thereof derived from biological tissue or fluid which forms a fibrin matrix. Alternatively, the fibrin glue may be formed from fibrinogen, or a derivative or metabolite thereof, or fibrin, produced by recombinant DNA technology.

The fibrin glue may also be formed by the interaction of fibrinogen and a catalyst of fibrin glue formation (such as thrombin and/or Factor XIII). As will be appreciated by those skilled in the art, fibrinogen is proteolytically cleaved in the presence of a catalyst (such as thrombin) and converted to a fibrin monomer. The fibrin monomers may then form polymers which may cross-link to form a fibrin glue matrix. The cross-linking of fibrin polymers may be enhanced by the presence of a catalyst such as Factor XIII. The catalyst of fibrin glue formation may be derived from blood plasma, cryoprecipitate or other plasma fractions containing fibrinogen or thrombin. Alternatively, the catalyst may be produced by recombinant DNA technology.

The rate at which the clot forms is dependent upon the concentration of thrombin mixed with fibrinogen. Being an enzyme dependent reaction, the higher the temperature (up to 37° C.) the faster the clot formation rate. The tensile strength of the clot is dependent upon the concentration of fibrinogen used.

Use of fibrin glue and methods for its preparation and use are described by Hirsh et al, in U.S. Pat. No. 5,643,192. Hirsh discloses the extraction of fibrinogen and thrombin components from a single donor, and the combination of only these components for use as a fibrin glue. Marx, U.S. Pat. No. 5,651,982, describes another preparation and method of use for fibrin glue. Marx provides a fibrin glue with liposomes for use as a topical sealant in mammals. The preparation and use of a topical fibrinogen complex (TFC) for wound healing is known in the field. PCT Application No. PCT/US95/15876, PCT Publication No. WO96/17633, of The American Red Cross discusses TFC preparations containing fibrinogen, thrombin, and calcium chloride, for example, at pages 16-18 of PCT Publication No. WO96/17633.

Several publications describe the use of fibrin glue for the delivery of therapeutic agents. For example, U.S. Pat. No. 4,983,393 discloses a composition for use as an intra-vaginal insert comprising agarose, agar, saline solution glycosaminoglycans, collagen, fibrin and an enzyme. Further, U.S. Pat. No. 3,089,815 discloses an injectable pharmaceutical preparation composed of fibrinogen and thrombin and U.S. Pat. No. 6,468,527 discloses a fibrin glue which facilitates the delivery of various biological and non-biological agents to specific sites within the body.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

The present invention will now be described in more detail with reference to the following non-limiting examples.

Example 1

Materials and Methods

Immunisation of Mice and Production of Antibody Secreting Hybridoma Cell Lines

VCAM-1/CD106 positive immunoselected ovine MPC were harvested and resuspended in 300 μl PBS supplemented with 20 μg muramyl dipeptide (Sigma Chemical Company, St. Louis, Mo.) as adjuvant. BALB/c mice were immunised intraperitoneally with 5×10⁶ BMSSC, and subsequently boosted a further 3 times at three-week intervals to ensure adequate affinity maturation of the immune response. Three days prior to fusion, 5×10⁶ cells resuspended in 100 µl PBS were administered via the tail vein. Immediately prior to fusion, mice were sacrificed and their spleens aseptically removed. Hybridomas secreting antibodies reactive with cultured BMSSC were made by fusing the NS1-Ag4-1 murine myeloma cell line and spleen cells derived from BALB/c mice immunised with trypsinised cultured ovine MPC. Fusion of splenocytes and myeloma cells was performed essentially as previously described (Filshie R J et al., 1998 and Zannettino A C et al., 1996).

Hybridomas were screened for their low reactivity with bone marrow mononuclear cells and reactivity with the primary immunogen (cultured ovine MPC) and human cultured MPC. The STRO-4 hybridoma was also selected for its reactivity and enrichment of ovine and human colony forming MPC(CFU-F).

Bone Marrow Samples

Normal human adult bone marrow aspirates were obtained under the approved guidelines of the Human Ethics Committee of the Royal Adelaide Hospital. Ovine bone marrow aspirates were obtained under the approved guidelines of the Animal ethic committee of the Institute of Medical and Veterinary Science. Ovine and human bone marrow mononuclear cells (BMMNC) were prepared by density gradient separation essentially as described previously (Gronthos S et al., 2003). The BMMNC preparations were used for immunomagnetic or -fluorescence activated cell sorting as described below.

MPC Cell Culture

Colony efficiency assays were performed at plating densities ranging from 0.1 to 1×10⁴ unfractionated or immunoselected BMMNC per cm² in triplicate 6-well plates over a 12 day period in triplicate wells as previously described. The cells were grown in α-MEM supplemented with 20% fetal calf serum, 2 mM L-glutamine and 100 µM L-ascorbate-2-phosphate 50 U/ml Penicillin, 50 µg/ml Streptomycin in 5% $CO_2$, at 37° C. humidified atmosphere, as previously described (Gronthos S et al., 2003). Colonies (cell clusters of >50 cells) were counted following fixation with 4% paraformaldehyde then stained with 0.1% toluidine blue. Primary BMSSC cultures were established by plating 1 to 5×10⁴ unfractionated or STRO-4⁺ immunoselected BMMNC per cm² and then grown in α-MEM as described above.

Differentiation Assays

To induce osteogenesis, MPC were cultured in α-MEM supplemented with 10% FCS, 100 µM L-ascorbate-2-phosphate, dexamethasone $10^{-7}$M and 3 mM inorganic phosphate, where mineralized deposits were identified by Alizarin Red staining (Gronthos S et al., 2003). Adipogenesis was induced in the presence of 0.5 mM isomethylbutylmethylxanthine (IBMX), 0.5 µM hydrocortisone, and 60 µM indomethacin, where Oil Red O staining was used to identify lipid-laden fat cells as previously described (Gronthos S et al., 2003). Chondrogenic differentiation was assessed in aggregate cultures treated with 10 ng/ml TGF-β3 and assessed by 0.1% Toluidine blue staining overnight to detect proteoglycan synthesis (Gronthos S et al., 2003).

Magnetic-Activated Cell Sorting (MACS)

This was performed as previously described (Gronthos S et al., 2003). In brief, approximately 1-3×10⁸ normal ovine or human BMMNC were incubated with anti-VCAM-1/CD106 or STRO-4 neat supernatant, for one hour on ice. The cell preparations were then incubated with goat anti-mouse IgG streptavidin microbeads and finally streptavidin FITC (1/50; Caltag Laboratories, Burlingame, Calif.) for 30 minutes on ice before being separated on a Mini MACS magnetic column (Miltenyi Biotec Inc., Auburn, Calif.) according to the manufacturers instructions.

Indirect Immunofluorescence and Flow Cytometric Analysis

Prior to immunolabelling, cultured cells (ovine MPC, human MPC, MG63, HOS, SAOS were incubated in blocking buffer (HBSS+20 mM Hepes, 1% normal human AB serum, 1% bovine serum albumin (BSA: Cohn fraction V, Sigma Aldrich Pty Ltd, NSW, Australia), and 5% FCS for 20 minutes on ice. Aliquots of 1×10⁵ cells were resuspended in 100 µL of supernatant of either STRO-4 for 45 minutes on ice. The isotype-matched, non-binding control antibodies, antibodies, $IgG_1$ (1B5) (kindly provided by Professor L. K. Ashman, University of Newcastle, AUS) was used as culture supernatant under identical conditions. The cells were then washed in HBSS with 5% FCS and incubated with a goat anti-mouse IgG (γ-chain specific) phycoerythrin (PE) (1/50; Southern Biotechnology Associates, Birmingham Ala.) for 45 minutes on ice. Prior to analysis, cells were washed twice in HBSS with 5% FCS and resuspended in PBS/1% paraformaldehyde. Flow cytometric analysis was performed using a Coulter Excel flow cytometer (Coulter Corp., Hialeah, Fla.). Positivity for each antibody was defined as the level of fluorescence greater than 99% of what was observed when isotype matched, non-binding control antibodies were used. 20,000 events were collected per sample as list mode data and analysed using Coulter ELITE software.

Immunoprecipitation and Western Blotting

Cell lysates were prepared as previously described. Goat anti-mouse Ig-coupled Dynabeads (Dynal, Oslo, Sweden), were washed twice in 1% (v/v) NP40-50 mM Tris-HCl, 150 mM NaCl, 1 mM EDTA [TSE] prior to the addition of neat STRO-4 supernatant and isotype matched non-binding control (1B5). This mixture was then incubated at 4° C. for a minimum of 6 hours, with rotation. The resulting pre-armed Dynabeads were washed twice in 1% NP40 TSE, and the beads collected using a magnetic particle collector (MPC-1, Dynal). To these, 1.0 ml aliquots of the appropriate NP40 cell lysate were added. The samples were incubated for 2 hours at 4° C. with rotation. The immunoprecipitates were then washed twice in 1% (v/v) NP40-TSE, once in 0.1% (v/v) NP40-TSE, and once in TSE, pH 8.0. The supernatant was then removed and samples stored at −20° C. or used immediately for electrophoresis. Each immunoprecipitate represented the material from 5×10⁶ cell equivalents. Samples were boiled for 3 minutes in 25 µL reducing sample buffer (62.5 mM Tris, 3% (w/v) SDS, 10% (v/v) glycerol and 5% (v/v) 2-mercaptoethanol) and analysed by 10% (w/v) SDS-polyacrylamide gel electrophoresis using Coomassie blue as previously described (Zannettino A C et al., 1996).

For mass spectrometry and protein sequencing, excised bands were subjected to 16 hours of tryptic digest at 37° C. The samples were then desalted and concentrated using a Millipore C18 ZipTip and a 1 µL aliquot was spotted onto a sample plate with 1 µL of matrix (α-cyano-4-hydroxycinnamic acid, 8 mg/mL in 70% v/v AcN, 1% v/v TFA) and allowed to air dry. Matrix assisted laser desorption ionisation (MALDI) mass spectrometry was performed with an Applied Biosystems 4700 Proteomics Analyser with TOF/TOF optics in MS mode. A Nd:YAG laser (355 nm) was used to irradiate the sample. The spectra were acquired in reflectron mode in the mass range 750 to 3500 Th. The data was exported in a format suitable for submission to the database search program Mascot (Matrix Science Ltd, London, UK).

For immunblots, proteins on unstained gels were transferred to Polyvinyl-difluoroacetate (PVDF; MSI Membranes, Geneworks, Adelaide, Australia) at 30 mA overnight in a wet blotting apparatus (Hoefer Scientific Instruments, San Francisco, Calif., USA). After blocking for 2 hours with 5% skim milk powder-0.05% Tween-20 in PBS, the filters were incubated with a polyclonal antibody to HSP-90 (Santa Cruz Biotechnologies) for 1 hour at room temperature. The primary antibody was subsequently detected with goat anti-mouse-alkaline phosphatase conjugate (Amersham Biosciences, Poole, UK) and immunoreactive proteins were visualised on a FluorImager (Molecular Dynamics, Sunnyvale, Calif.) using ImageQuant software (Molecular Dynamics) as recommended by the manufacturer (Zannettino A C et al., 1996 and Shi S et al., 2001).

Example 2

Figure 1:
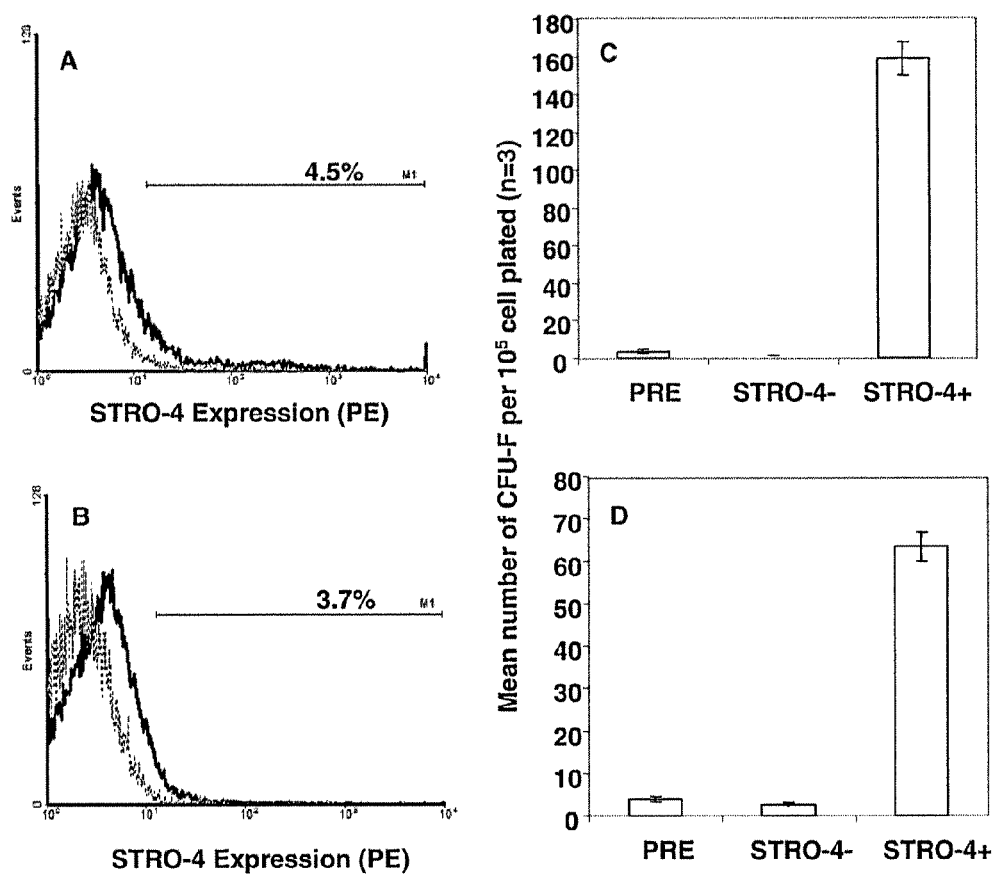
FIG. 1. STRO-4 Antigen is Expressed by a Minor Population of Ovine and Human BM MNC that Includes Essentially all Clonogenic MPC.

Generation of the Monoclonal Antibody STRO-4 that Identifies Ovine and Human MPC A panel of mouse monoclonal antibodies (mAb) reactive with ovine MPC were generated following the fusion of splenocytes derived from mice immunized with cultured VCAM-1/CD106 positive derived ovine MPC with the myeloma cell line, NS1-Ag4-1, as described in the methods. Preliminary screens were designed to identify mAbs which reacted with both ovine and human clonogenic MPC(CFU-F). One such hybridoma, STRO-4, was selected for further analysis as it identified a minor subset of ovine and human bone marrow mononuclear cells (FIGS. 1A and B) and efficiently isolated ovine and human CFU-F (FIGS. 1C and D). Ex vivo expanded ovine and human MPC maintained high cell surface expression of the antigen identified by STRO-4 (FIGS. 2A and B) and exhibited the capacity for multi-lineage differentiation into osteoblasts, adipocytes and chondrocytes (FIG. 3). The immunoglobulin isotype of STRO-4 from tertiary hybridoma supernatants was determined to be IgG1 using an isotype detection kit as described in the methods.

Example 3

Characterisation of the Antigen Recognised by STRO-4

Immunoprecipitation was used to purify the STRO-4 antigen from the immature human osteosarcoma cell line, MG63, which expressed high cell surface levels of the STRO-4 antigen (FIG. 2C). Human MG63 plasma membrane proteins were extracted with 1% NP40 as described in the methods, and incubated with the STRO-4 antibody. The STRO-4 immunoprecipitated protein was recovered using sheep anti-mouse IgG antibodies conjugated to magnetic Dynal beads and resolved by SDS-polyacrylamide gel electrophoresis (SDS-PAGE) as described in the methods. Coomassie Blue staining of resolved immunoprecipitates revealed a specific peptide band with an apparent molecular mass of 90 kDa (FIG. 4). The 90 kDa protein fragment was excised from the gel and prepared for mass spectrometry and amino acid sequence analysis. The resultant STRO-4 peptide sequences were used to survey the Protein database at the National Center for Biotechnology Information and found to exhibit homology with the human heat shock protein-90 beta (accession number, P08238) (FIG. 5).

To confirm that the STRO-4 reactive 90 kDa peptide was HSP-90beta, whole cell lysates and STRO-4 immunoprecipitated extracts were resolved by SDS-PAGE. Western blot analysis was performed using a commercially available rabbit polyclonal antibody reactive with human HSP-90 beta as described in the methods. The STRO-4-immunoprecipitates exhibited specific reactivity with the HSP-90-specific antibody at the appropriate molecular weight of 90 kDa (FIG. 6).

In the present study, the ovine and human MPC populations selected on the basis of STRO-4 cell surface expression demonstrated extensive proliferation in vitro, while retaining their capacity for differentiation into bone, cartilage and adipose tissues. Thus far, there have been few antibody reagents which exhibit cross reactivity between different species.

Thus antibodies to STRO-4 may be used as an effective means of isolating and enriching MPCs.

REFERENCES

Airey J A, Almeida-Porada G, Colletti E J, Porada C D, Chamberlain J, Movsesian M, Sutko J L, Zanjani E D (2004) Human mesenchymal stem cells form Purkinje fibers in fetal sheep heart. Circulation 109(11):1401-7.

Anseth K S et al. (2002) In situ forming degradable networks and their application in tissue engineering and drug delivery 78(103):199-209.

Bregni et al. (1992). Human peripheral blood hematopoietic progenitors are optimal targets of retroviral-mediated gene transfer. Blood 80, 1418-22.

Chen B, Piel W H, Gui L, Bruford E, Monteiro A (2005) The HSP90 family of genes in the human genome: insights into their divergence and evolution. Genomics 86(6):627-37.

Cole et al. (1984) Human monoclonal antibodies. *Mol. Cell. Biochem* 62, 109-20.

Cote et al. (1983) Generation of human monoclonal antibodies reactive with cellular antigens. *Proc. Natl. Acad. Sci. USA* 80, 2026-30.

Danos et al. (1988) Safe and efficient generation of recombinant retroviruses with amphotropic and ecotropic host ranges. *Proc. Nod. Acad. Sci. USA*. 85, 6460-4

Filshie R J, Zannettino A C, Makrynikola V, Gronthos S, Henniker A J, Bendall L J, Gottlieb D J, Simmons P J, Bradstock K F (1998) MUC18, a member of the immunoglobulin superfamily, is expressed on bone marrow fibroblasts and a subset of hematological malignancies. Leukemia 12(3):414-21.

Finer et al. (1994) kat: a high-efficiency retroviral transduction system for primary human T lymphocytes. *Blood.* 83, 43-50.

Frey et al. (1998) High-efficiency gene transfer into ex vivo expanded human hematopoietic progenitors and precursor cells by adenovirus vectors. *Blood* 91, 2781-92.

Gronthos et al. (1994). The STRO-1+ fraction of adult human bone marrow contains the osteogenic precursors. *Blood* 84, 4164-73.

Gronthos S, Zannettino A C, Hay S J, Shi S, Graves S E, Kortesidis A, Simmons P J (2003) Molecular and cellular characterisation of highly purified stromal stem cells derived from human bone marrow. J Cell Sci 116(Pt 9):1827-35.

Kohler et al. (1975). Continuous cultures of fused cells secreting antibody of predefined specificity. *Nature* 256, 495-7.

Kozbor et al. (1985). Specific immunoglobulin production and enhanced tumorigenicity following ascites growth of human hybridomas. J. Immunol. Methods 81, 31-42.

Liechty K W, MacKenzie T C, Shaaban A F, Radu A, Moseley A M, Deans R, Marshak D R, Flake A W (2000) Human mesenchymal stem cells engraft and demonstrate site-specific differentiation after in utero transplantation in sheep. Nat Med 6(11):1282-6.

Mackenzie T C, Flake A W (2001) Human mesenchymal stem cells persist, demonstrate site-specific multipotential differentiation, and are present in sites of wound healing and tissue regeneration after transplantation into fetal sheep. Blood Cells Mol Dis 27(3):601-4.

Miller et al. (1986) Redesign of retrovirus packaging cell lines to avoid recombination leading to helper virus production. *Mol Cell Biol.* 6, 2895-902.

Miller et al. (1989) Improved retroviral vectors for gene transfer and expression. *Biotechniques.* 7, 980-82, 984-86, 989-990.

Pear et al. (1993) Production of High-Titer Helper-Free Retroviruses by Transient Transfection. *Proc Natl Acad Sci USA.* 90, 8392-8396.

Pearson W R and Lipman D J (1988) Improved tools for biological sequence comparison. 85(8):2444-8.

Rucker et al. (1996) Regions in beta-chemokine receptors CCR5 and CCR2b that determine HIV-1 cofactor specificity. *Cell* 87, 437-46.

Shi S, Robey P G, Gronthos S (2001) Comparison of human dental pulp and bone marrow stromal stem cells by cDNA microarray analysis. Bone 29(6):532-9.

Shi S, Gronthos S (2003) Perivascular niche of postnatal mesenchymal stem cells in human bone marrow and dental pulp. J Bone Miner Res 18(4):696-704.

Simmons P J, Torok-Storb B (1991) Identification of stromal cell precursors in human bone marrow by a novel monoclonal antibody, STRO-1. Blood 78(1):55-62.

Voss A K, Thomas T. Gruss P (2000) Mice lacking HSP90beta fail to develop a placental labyrinth. Development 127(1):1-11, Yamada T, Hashiguchi A, Fukushima S. Kakita Y, Umezawa A. Maruyama T, Hata J (2000) Function of 90-kDa heat shock protein in cellular differentiation of human embryonal carcinoma cells. In Vitro Cell Dev Biol Anim 36(2): 139-46.

Zannettino A C, Rayner J R, Ashman L K, Gonda Ti. Simmons P J (1996) A powerful new technique for isolating genes encoding cell surface antigens using retroviral expression cloning. J Immunol 156(2):611-20, Xu et al. (1994). Correction of the enzyme deficiency in hematopoietic cells of Gaucher patients using a clinically acceptable retroviral supernatant transduction protocol. *Exp. Hemat.* 22, 223-30.

---

The invention claimed is:

1. A method of enriching a sample of cells for adult multipotential cells, the method comprising preparing a cell sample from a tissue source and enriching for adult multipotential cells that express the HSP-90beta marker using a HSP-90beta binding agent or antigen binding fragment thereof, wherein the HSP-90beta binding agent is a STRO-4 monoclonal antibody or antigen-binding fragment or derivative thereof or an antibody or antigen binding fragment thereof having the same specificity as the STRO-4 monoclonal antibody.

2. A method according to claim 1, wherein enriching for cells that express the HSP-90beta marker comprises:
   contacting a cell sample with the HSP-90beta binding agent; and
   separating cells bound to the HSP-90beta binding agent from cells that do not bind the HSP-90beta binding agent.

3. A method according to claim 1 or 2, wherein the HSP-90beta binding agent or antigen binding fragment or derivative thereof is selected from the group consisting of:

(i) a STRO-4 monoclonal antibody;
(ii) a chimeric antibody comprising heavy and light chain variable regions from STRO-4 and human heavy and light chain constant regions; and
(iii) a humanized antibody comprising at least one complementarity determining region (CDR) from STRO-4 and human framework and constant region sequences.

4. A method according to claim 1 or 2, wherein the HSP-90beta binding agent or antigen binding fragment or derivative thereof is a STRO-4 antibody or an antigen-binding fragment of the STRO-4 antibody and wherein the STRO-4 antibody is produced by the hybridoma cell line deposited with ATCC on 10 Jul. 2008 under the provisions of the Budapest Treaty under deposit accession number PTA-9362.

5. A method according to claim 1, wherein the cell sample is derived from placenta, adipose tissue, teeth, dental pulp, skin, liver, kidney, heart, retina, brain, hair follicles, intestine, lung, spleen, lymph node, thymus, ovary, pancreas, bone, ligament, bone marrow, tendon or skeletal muscle.

* * * * *

SEQUENCE LISTING

```
<160> NUMBER OF SEQ ID NOS: 1

<210> SEQ ID NO 1
<211> LENGTH: 723
<212> TYPE: PRT
<213> ORGANISM: Homo sapiens

<400> SEQUENCE: 1

Pro Glu Glu Val His His Gly Glu Glu Val Glu Thr Phe Ala Phe
1               5                   10                  15

Gln Ala Glu Ile Ala Gln Leu Met Ser Leu Ile Ile Asn Thr Phe Tyr
            20                  25                  30

Ser Asn Lys Glu Ile Phe Leu Arg Glu Leu Ile Ser Asn Ala Ser Asp
        35                  40                  45

Ala Leu Asp Lys Ile Arg Tyr Glu Ser Leu Thr Asp Pro Ser Lys Leu
    50                  55                  60

Asp Ser Gly Lys Glu Leu Lys Ile Asp Ile Ile Pro Asn Pro Gln Glu
65                  70                  75                  80

Arg Thr Leu Thr Leu Val Asp Thr Gly Ile Gly Met Thr Lys Ala Asp
                85                  90                  95

Leu Ile Asn Asn Leu Gly Thr Ile Ala Lys Ser Gly Thr Lys Ala Phe
            100                 105                 110

Met Glu Ala Leu Gln Ala Gly Ala Asp Ile Ser Met Ile Gly Gln Phe
        115                 120                 125

Gly Val Gly Phe Tyr Ser Ala Tyr Leu Val Ala Glu Lys Val Val Val
    130                 135                 140

Ile Thr Lys His Asn Asp Asp Glu Gln Tyr Ala Trp Glu Ser Ser Ala
145                 150                 155                 160

Gly Gly Ser Phe Thr Val Arg Ala Asp His Gly Glu Pro Ile Gly Arg
                165                 170                 175

Gly Thr Lys Val Ile Leu His Leu Lys Glu Asp Gln Thr Glu Tyr Leu
            180                 185                 190

Glu Glu Arg Arg Val Lys Glu Val Val Lys Lys His Ser Gln Phe Ile
        195                 200                 205

Gly Tyr Pro Ile Thr Leu Tyr Leu Glu Lys Glu Arg Glu Lys Glu Ile
    210                 215                 220
```

-continued

```
Ser Asp Asp Glu Ala Glu Glu Lys Gly Glu Lys Glu Glu Asp
225                 230                 235                 240

Lys Asp Asp Glu Glu Lys Pro Lys Ile Glu Asp Val Gly Ser Asp Glu
                245                 250                 255

Glu Asp Asp Ser Gly Lys Asp Lys Lys Lys Thr Lys Lys Ile Lys
                260                 265                 270

Glu Lys Tyr Ile Asp Gln Glu Leu Asn Lys Thr Lys Pro Ile Trp
        275                 280                 285

Thr Arg Asn Pro Asp Asp Ile Thr Gln Glu Glu Tyr Gly Glu Phe Tyr
        290                 295                 300

Lys Ser Leu Thr Asn Asp Trp Glu Asp His Leu Ala Val Lys His Phe
305                 310                 315                 320

Ser Val Glu Gly Gln Leu Glu Phe Arg Ala Leu Leu Phe Ile Pro Arg
                325                 330                 335

Arg Ala Pro Phe Asp Leu Phe Glu Asn Lys Lys Lys Asn Asn Ile
                340                 345                 350

Lys Leu Tyr Val Arg Arg Val Phe Ile Met Asp Ser Cys Asp Glu Leu
        355                 360                 365

Ile Pro Glu Tyr Leu Asn Phe Ile Arg Gly Val Val Asp Ser Glu Asp
370                 375                 380

Leu Pro Leu Asn Ile Ser Arg Glu Met Leu Gln Gln Ser Lys Ile Leu
385                 390                 395                 400

Lys Val Ile Arg Lys Asn Ile Val Lys Lys Cys Leu Glu Leu Phe Ser
                405                 410                 415

Glu Leu Ala Glu Asp Lys Glu Asn Tyr Lys Lys Phe Tyr Glu Ala Phe
                420                 425                 430

Ser Lys Asn Leu Lys Leu Gly Ile His Glu Asp Ser Thr Asn Arg Arg
        435                 440                 445

Arg Leu Ser Glu Leu Leu Arg Tyr His Thr Ser Gln Ser Gly Asp Glu
        450                 455                 460

Met Thr Ser Leu Ser Glu Tyr Val Ser Arg Met Lys Glu Thr Gln Lys
465                 470                 475                 480

Ser Ile Tyr Tyr Ile Thr Gly Glu Ser Lys Glu Gln Val Ala Asn Ser
                485                 490                 495

Ala Phe Val Glu Arg Val Arg Lys Arg Gly Phe Glu Val Val Tyr Met
                500                 505                 510

Thr Glu Pro Ile Asp Glu Tyr Cys Val Gln Gln Leu Lys Glu Phe Asp
        515                 520                 525

Gly Lys Ser Leu Val Ser Val Thr Lys Glu Gly Leu Glu Leu Pro Glu
        530                 535                 540

Asp Glu Glu Glu Lys Lys Met Glu Glu Ser Lys Ala Lys Phe Glu
545                 550                 555                 560

Asn Leu Cys Lys Leu Met Lys Glu Ile Leu Asp Lys Lys Val Glu Lys
                565                 570                 575

Val Thr Ile Ser Asn Arg Leu Val Ser Ser Pro Cys Cys Ile Val Thr
                580                 585                 590

Ser Thr Tyr Gly Trp Thr Ala Asn Met Glu Arg Ile Met Lys Ala Gln
        595                 600                 605

Ala Leu Arg Asp Asn Ser Thr Met Gly Tyr Met Met Ala Lys Lys His
        610                 615                 620

Leu Glu Ile Asn Pro Asp His Pro Ile Val Glu Thr Leu Arg Gln Lys
625                 630                 635                 640
```

-continued

```
Ala Glu Ala Asp Lys Asn Asp Lys Ala Val Lys Asp Leu Val Val Leu
                 645             650             655

Leu Phe Glu Thr Ala Leu Leu Ser Ser Gly Phe Ser Leu Glu Asp Pro
             660             665             670

Gln Thr His Ser Asn Arg Ile Tyr Arg Met Ile Lys Leu Gly Leu Gly
         675             680             685

Ile Asp Glu Asp Glu Val Ala Ala Glu Glu Pro Asn Ala Ala Val Pro
         690             695             700

Asp Glu Ile Pro Pro Leu Glu Gly Asp Glu Asp Ala Ser Arg Met Glu
705             710             715             720

Glu Val Asp
```